(12) United States Patent
Cooper et al.

(10) Patent No.: US 6,309,884 B1
(45) Date of Patent: Oct. 30, 2001

(54) INDIVIDUAL CALIBRATION OF BLOOD GLUCOSE FOR SUPPORTING NONINVASIVE SELF-MONITORING BLOOD GLUCOSE

(75) Inventors: Patrick J. Cooper, Indiana, PA (US); Todd Q. Barker, Pleasanton, CA (US)

(73) Assignee: Diasense, Inc., Pittsburgh, PA (US)

( * ) Notice: Subject to any disclaimer, the term of this patent is extended or adjusted under 35 U.S.C. 154(b) by 0 days.

(21) Appl. No.: 09/367,625

(22) PCT Filed: Feb. 26, 1998

(86) PCT No.: PCT/US98/03762

§ 371 Date: Dec. 8, 1999

§ 102(e) Date: Dec. 8, 1999

(87) PCT Pub. No.: WO98/37805

PCT Pub. Date: Sep. 3, 1998

Related U.S. Application Data

(60) Provisional application No. 60/039,165, filed on Feb. 26, 1997.

(51) Int. Cl.[7] ............................................................ G01N 31/00
(52) U.S. Cl. ............................ 436/14; 436/8; 436/164; 435/14; 600/310; 600/316; 600/365; 356/39; 702/22; 702/23
(58) Field of Search ............................. 436/8, 14, 164, 436/171; 435/14; 600/365, 310, 316, 322; 702/19, 22, 23, 27, 28; 356/39

(56) References Cited

U.S. PATENT DOCUMENTS

| | | | |
|---|---|---|---|
| 5,028,787 | * 7/1991 | Rosenthal et al. | 250/339.12 |
| 5,068,536 | * 11/1991 | Rosenthal | 250/341.5 |
| 5,070,874 | 12/1991 | Barnes et al. | 600/316 |
| 5,077,476 | * 12/1991 | Rosenthal | 250/339.04 |
| 5,204,532 | * 4/1993 | Rosenthal | 250/341.5 |
| 5,313,941 | * 5/1994 | Braig et al. | 600/322 |
| 5,329,931 | 7/1994 | Clauson et al. | 600/323 |
| 5,341,805 | 8/1994 | Stavridi et al. | 600/316 |
| 5,360,004 | 11/1994 | Purdy et al. | 600/310 |
| 5,361,758 | * 11/1994 | Hall et al. | 600/322 |
| 5,370,114 | * 12/1994 | Wong et al. | 600/322 |
| 5,379,764 | 1/1995 | Barnes et al. | 600/473 |
| 5,433,197 | * 7/1995 | Stark | 600/319 |
| 5,460,177 | 10/1995 | Purdy et al. | 600/436 |
| 5,471,981 | 12/1995 | Wiggins et al. | 600/309 |
| 5,725,480 | * 3/1998 | Oosta et al. | 600/310 |
| 6,088,605 | * 7/2000 | Griffith et al. | 600/316 |

* cited by examiner

Primary Examiner—Maureen M. Wallenhorst
(74) Attorney, Agent, or Firm—Webb Ziesenheim Logsdon Orkin & Hanson, P.C.

(57) ABSTRACT

A method is provided for calibrating a noninvasive glucose monitor for prospective noninvasive glucose determination. Spectroscopic transflectance readings are measured on the patient's skin using a noninvasive glucose monitor. The patient's blood glucose level is measured with an invasive glucose monitor. The noninvasive and invasive measurements are correlated to form an individual algorithm for each patient. Preferably, the position of the patient's skin with respect to the probe of the noninvasive monitor is spatially adjusted while collecting the transflectance measurements such that multiple readings are taken on the patient's skin. The measurements are preferably taken over a period of time and over a plurality of glucose levels in the patient.

20 Claims, 19 Drawing Sheets

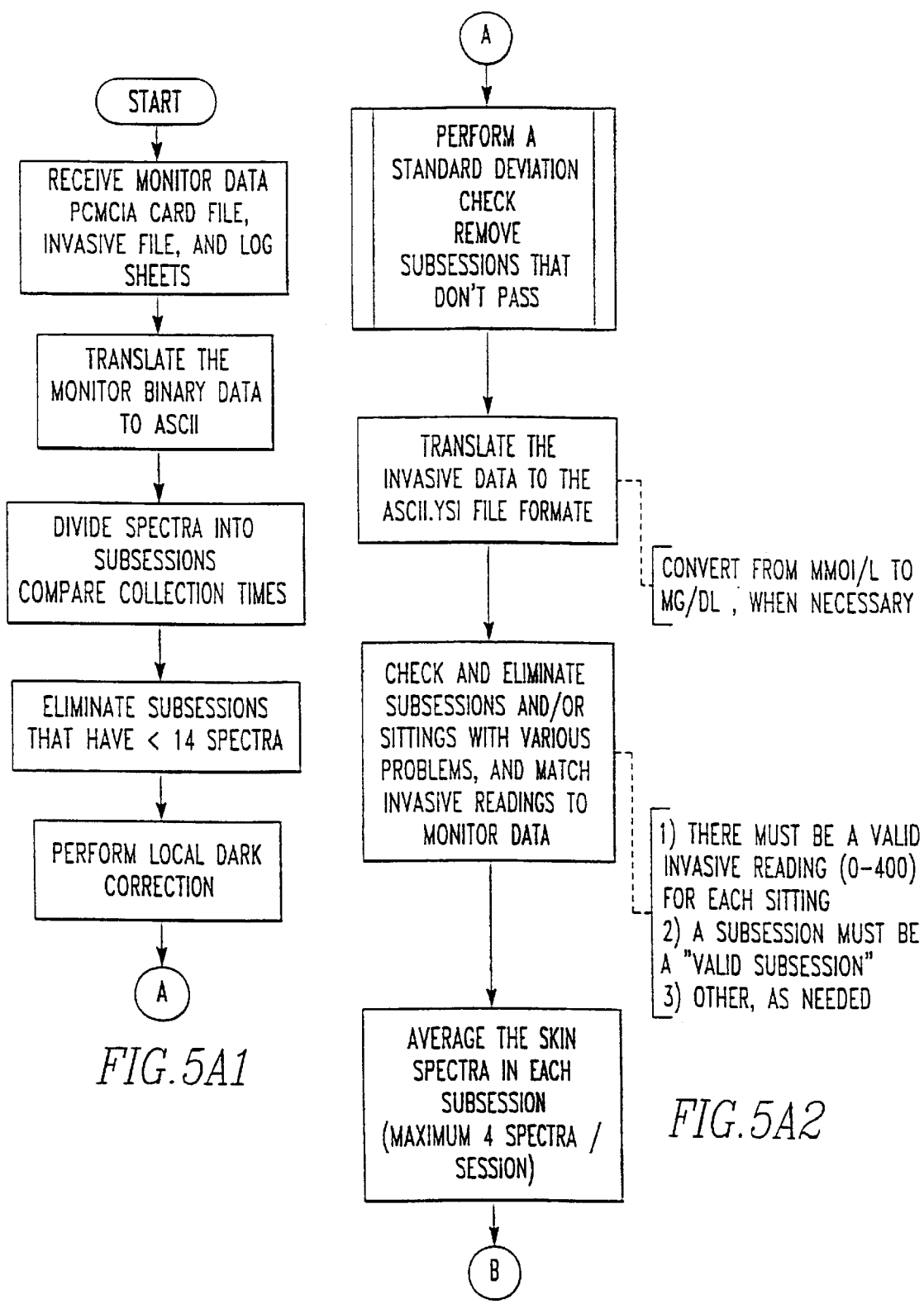
FIG.5A1     FIG.5A2

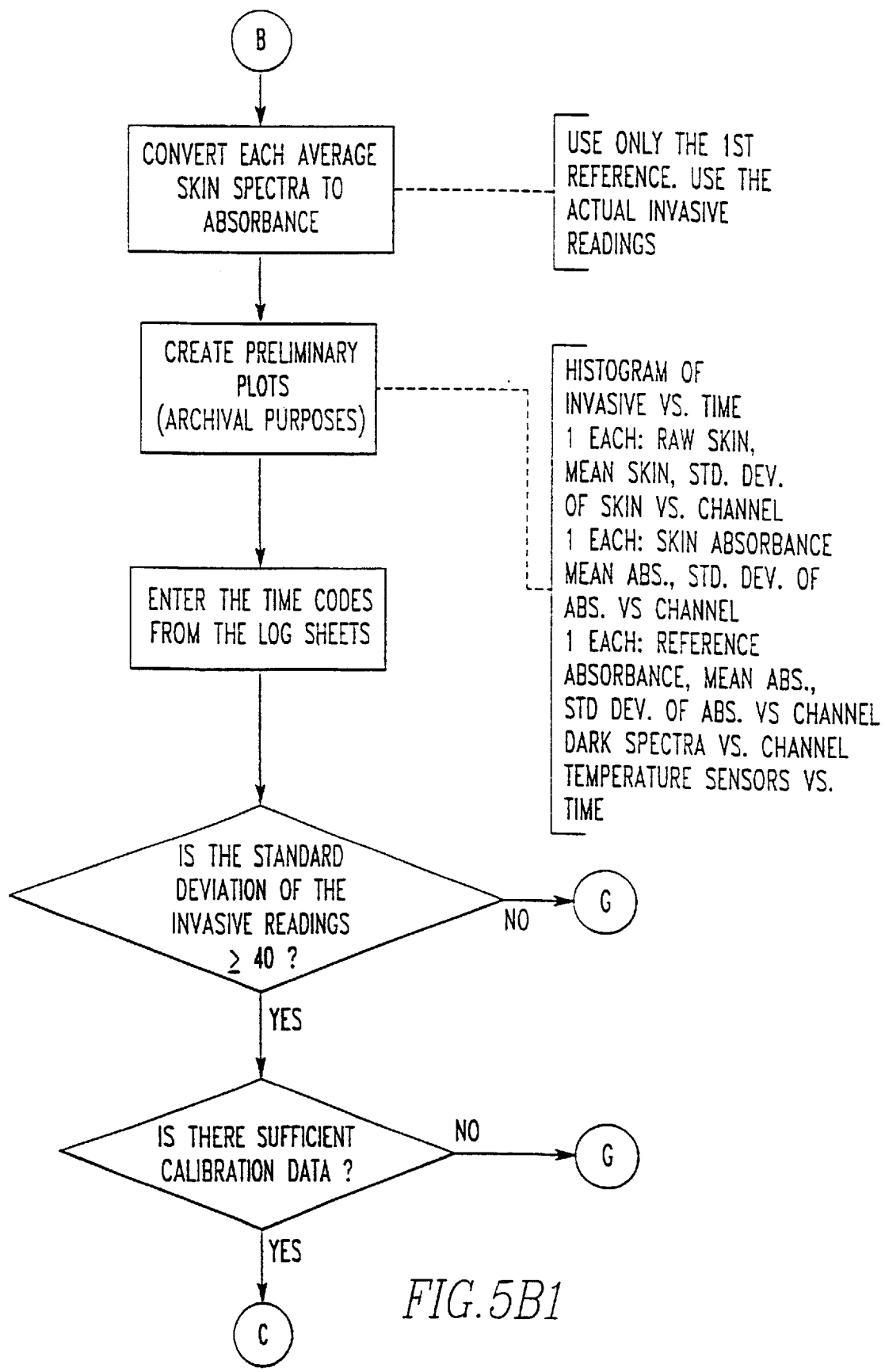
FIG.5B1

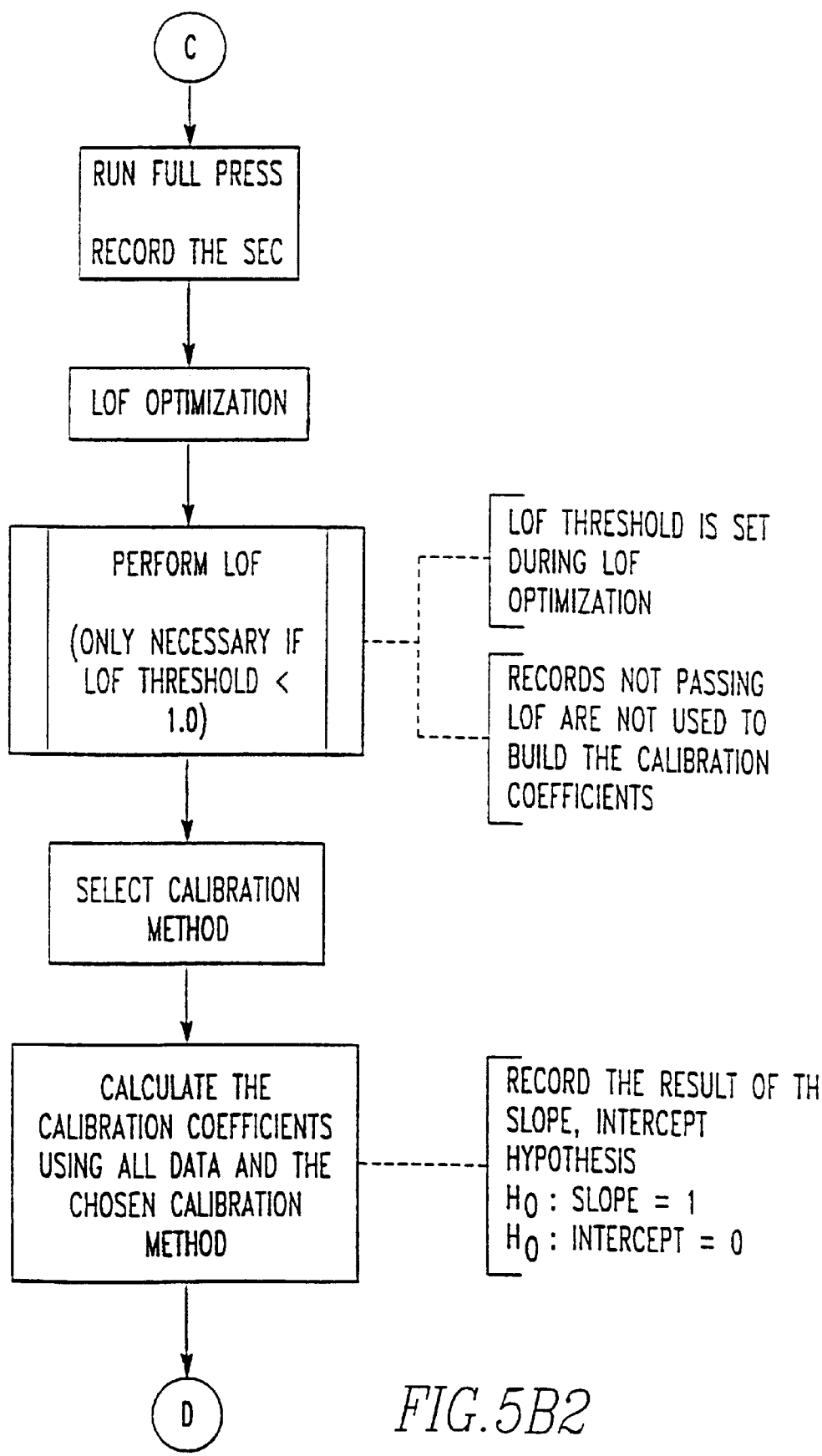
FIG.5B2

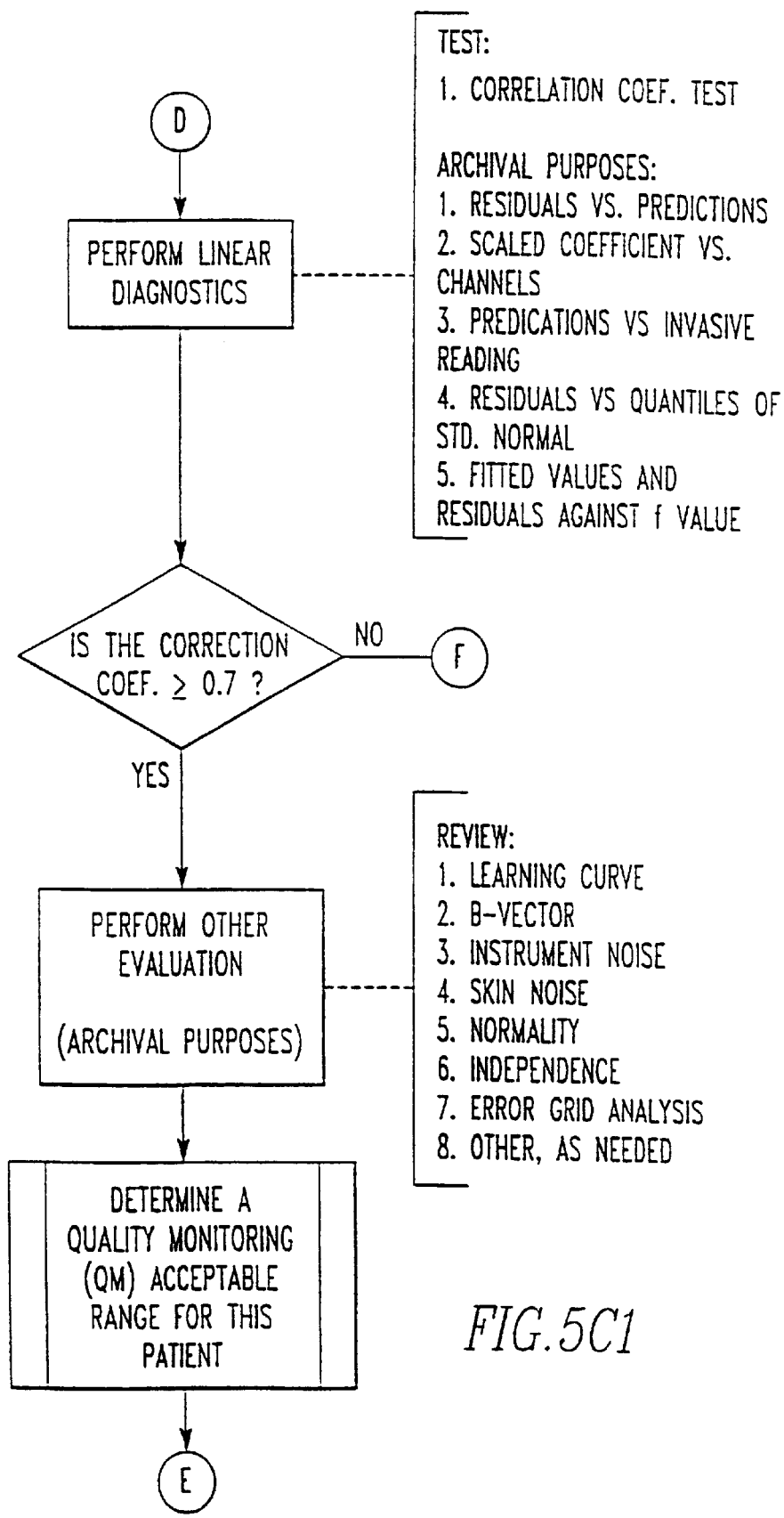
FIG.5C1

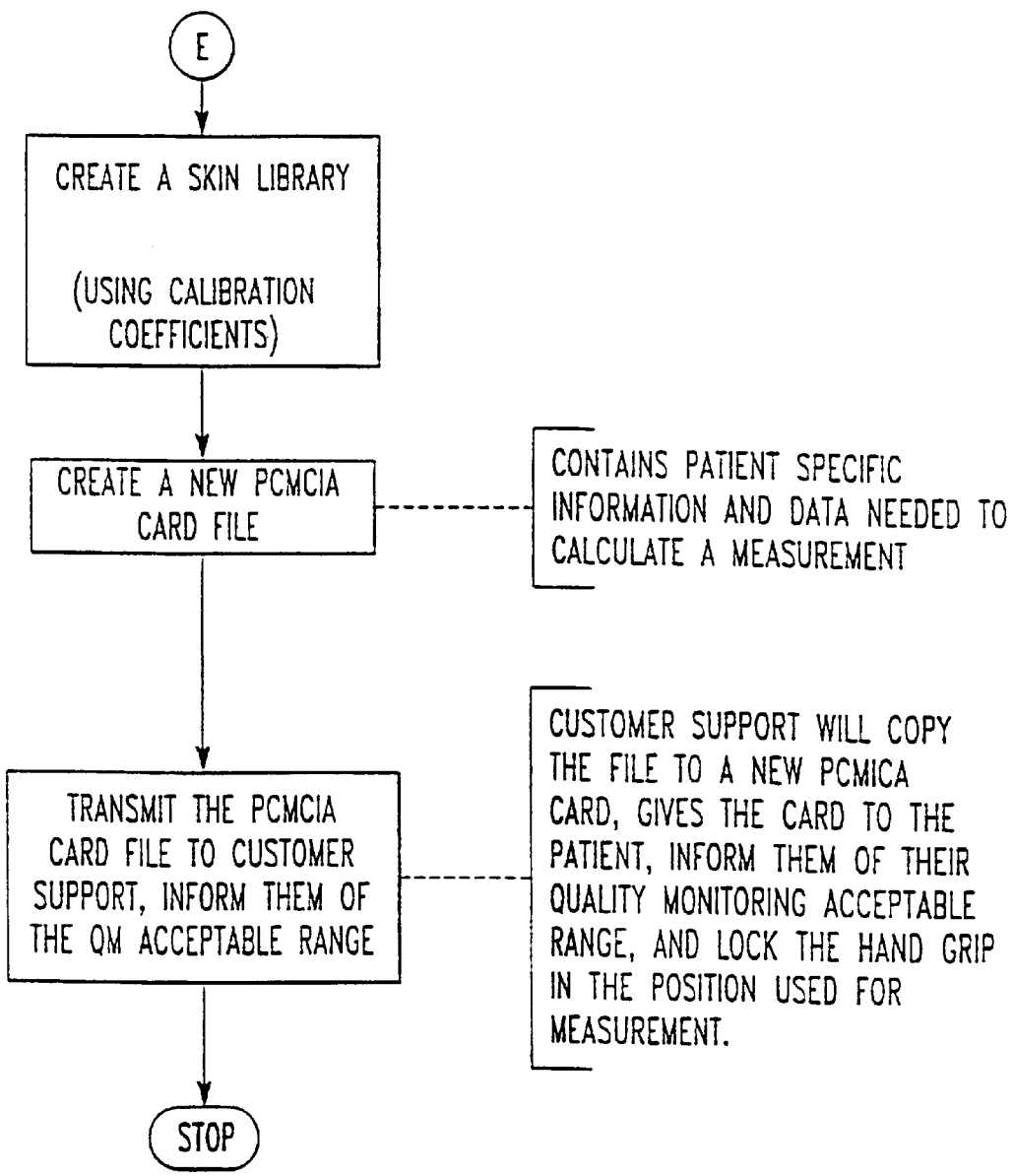
FIG.5C2

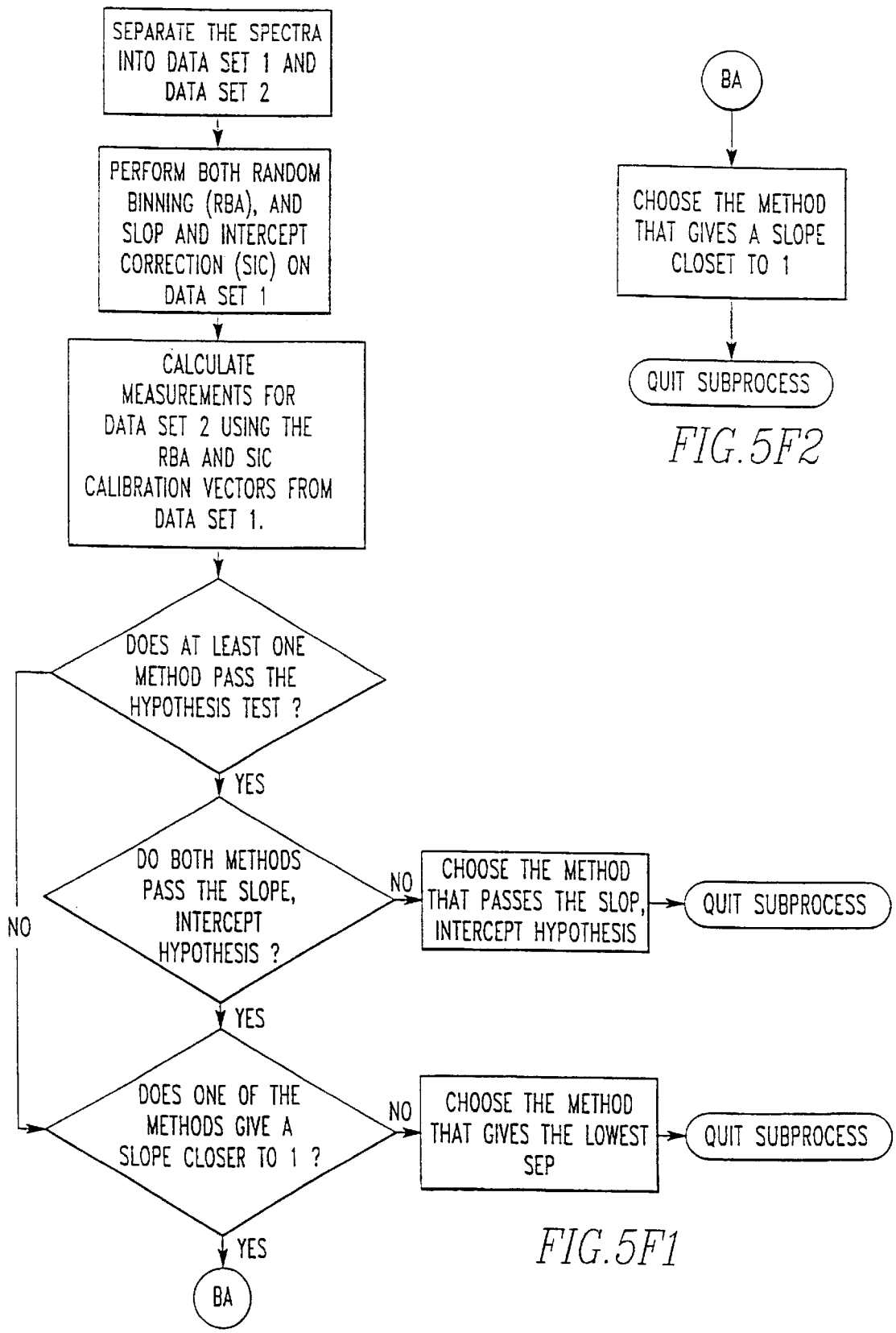

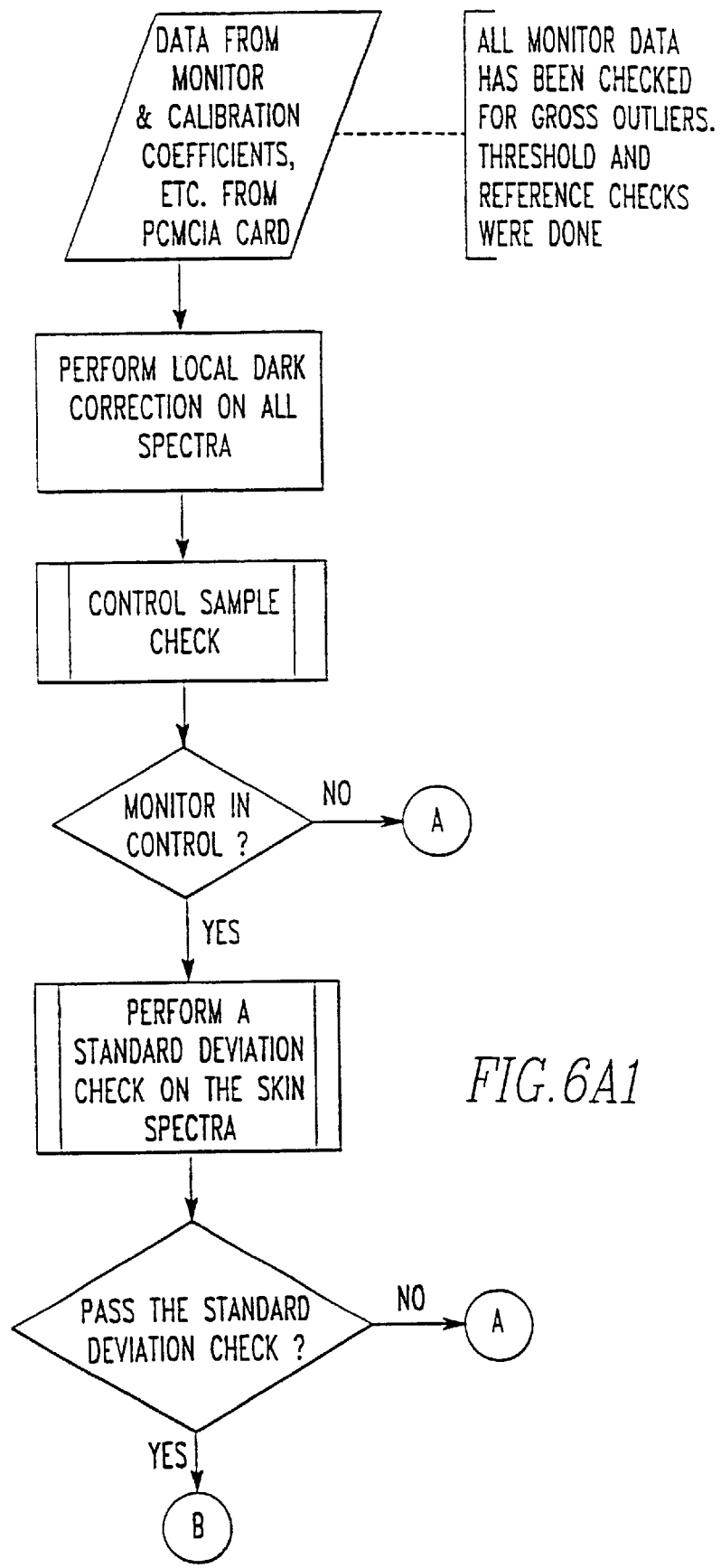
FIG.6A1

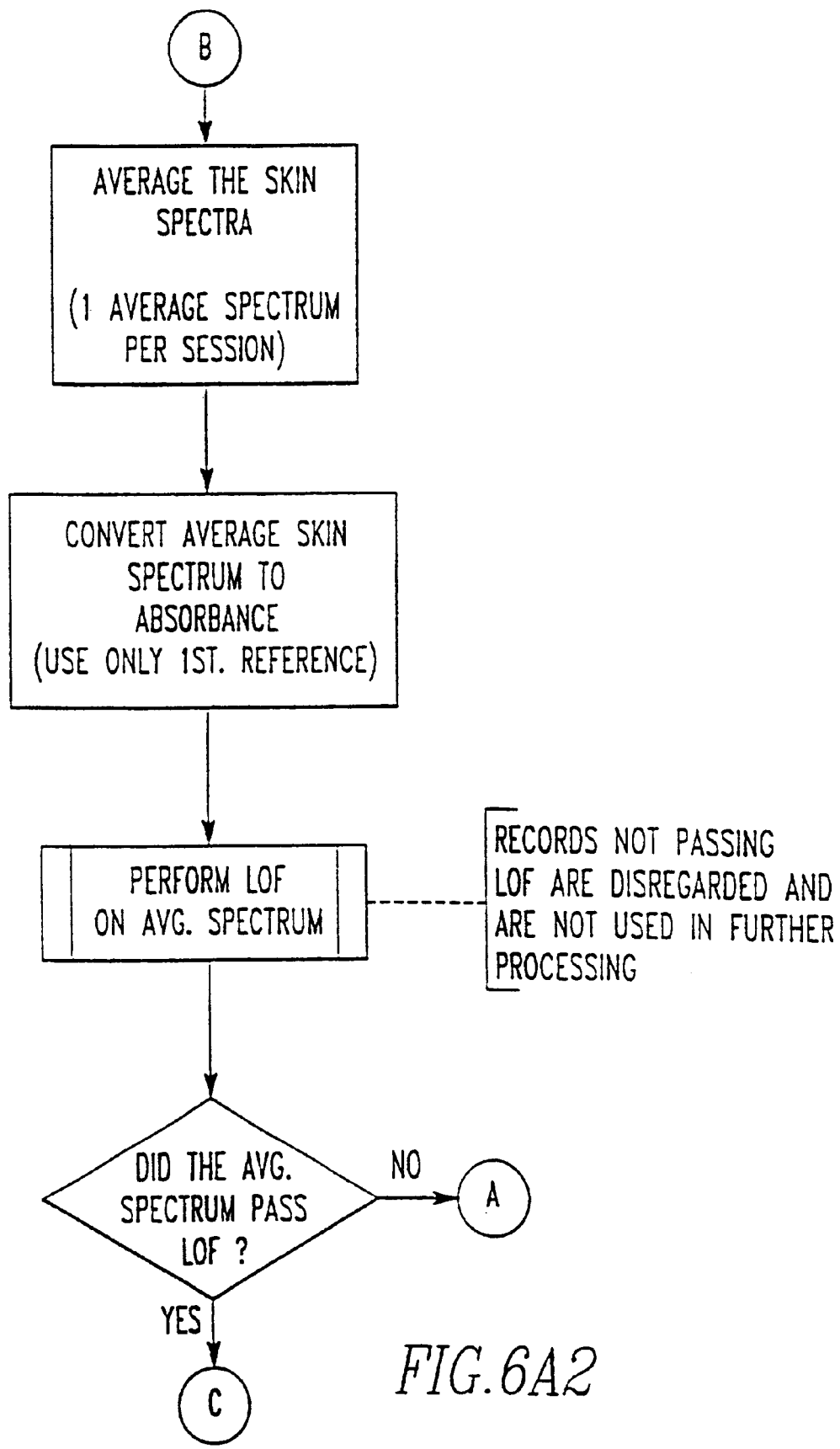
FIG.6A2

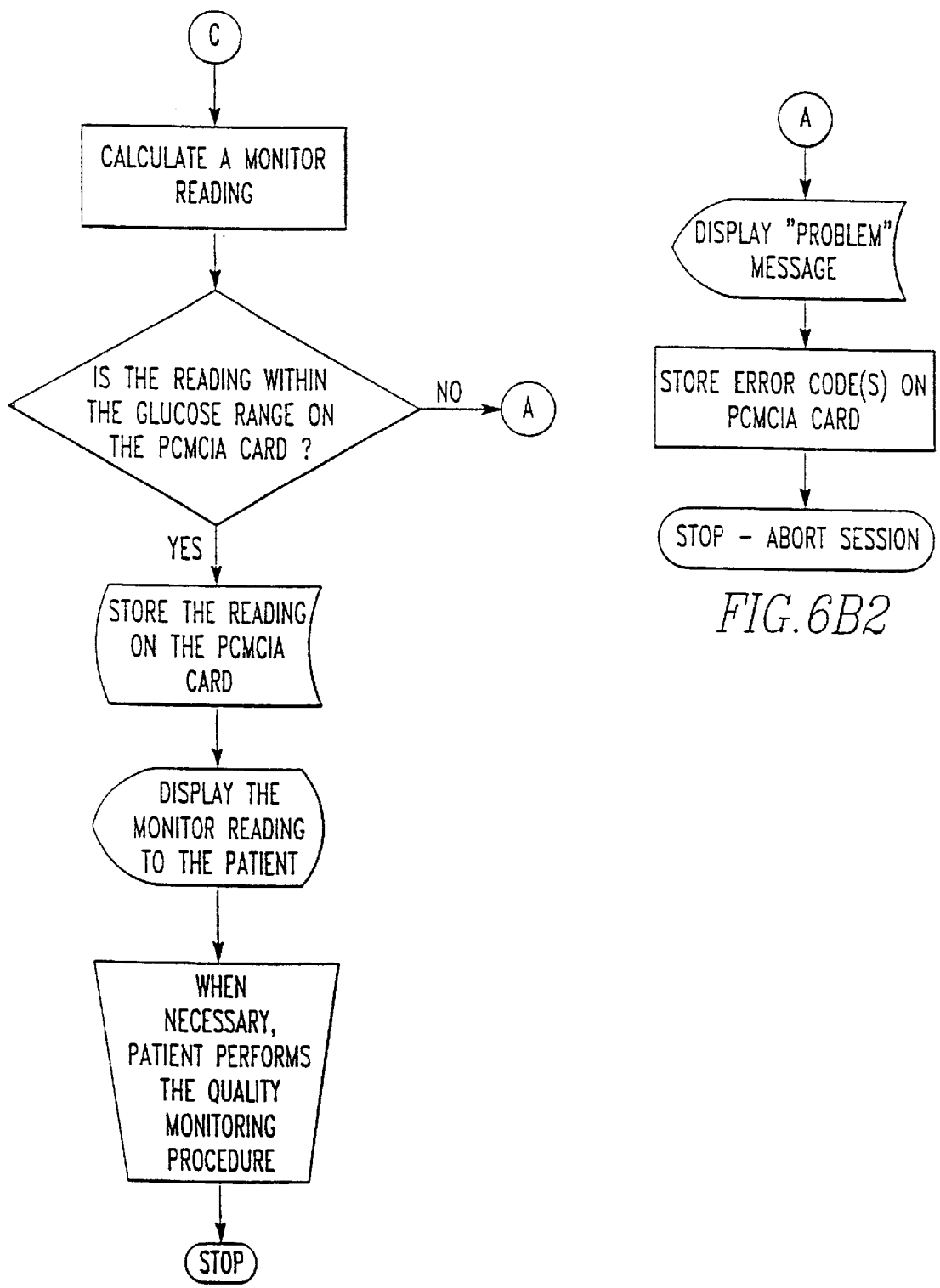
FIG.6B1
FIG.6B2

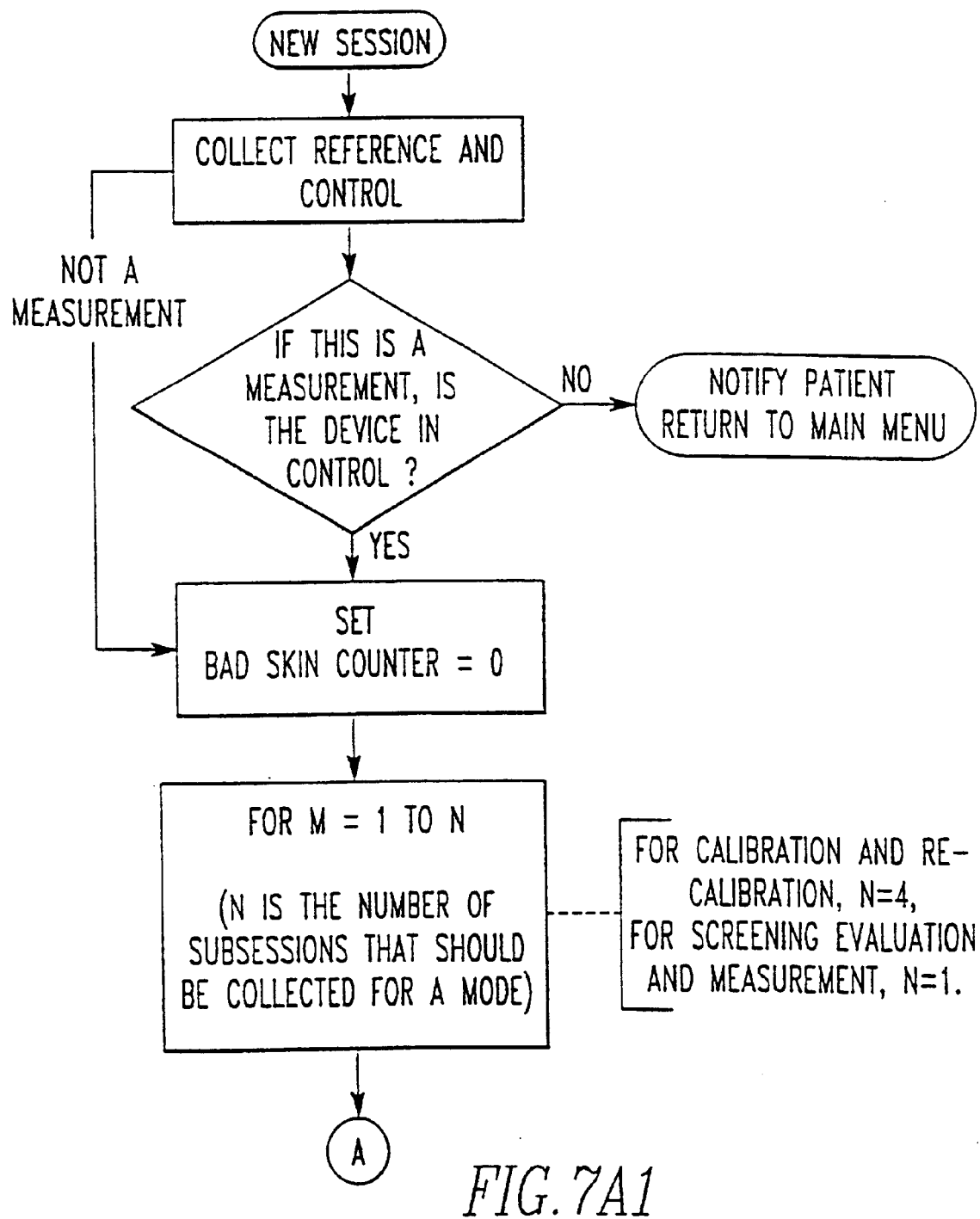
FIG. 7A1

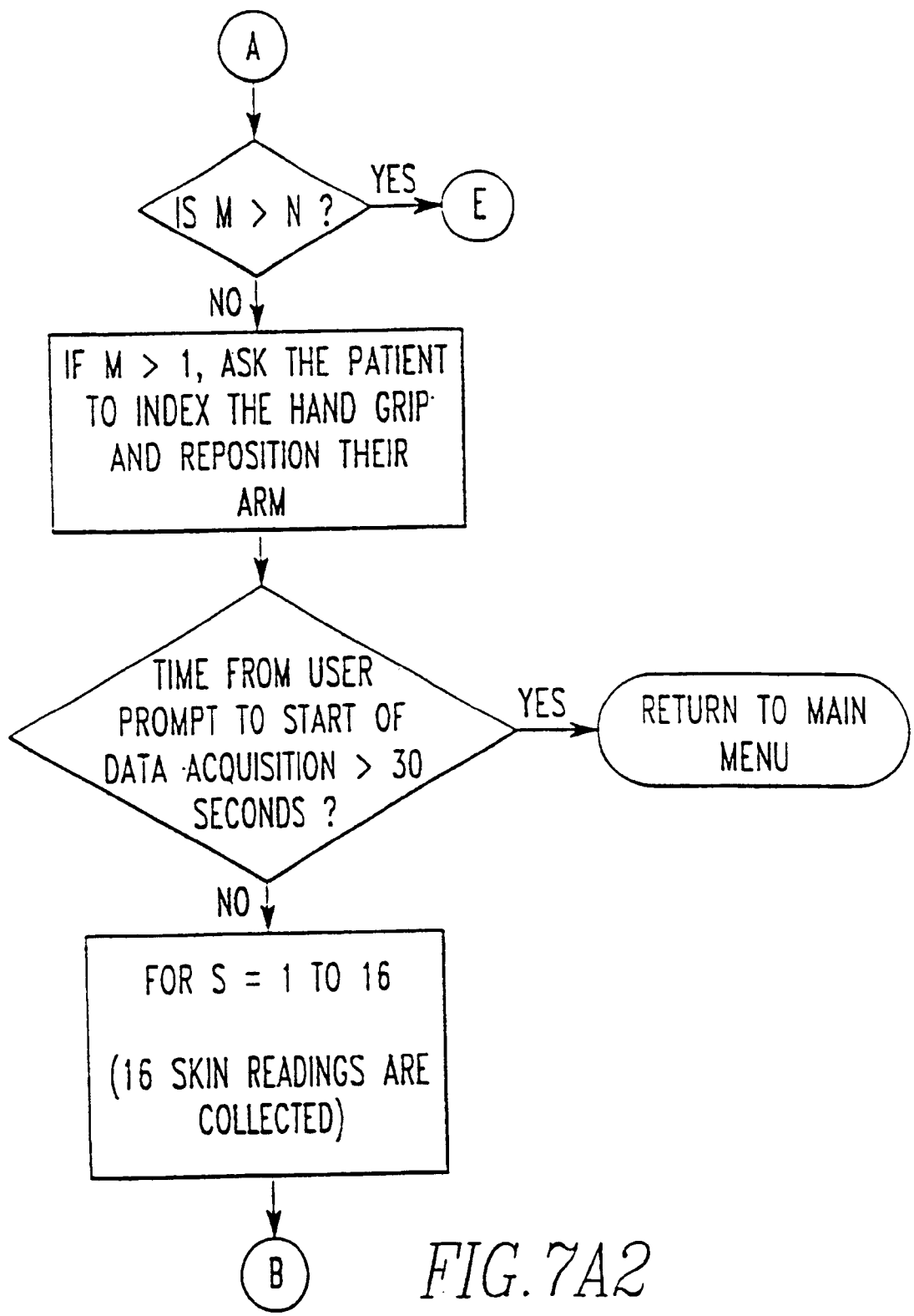
FIG. 7A2

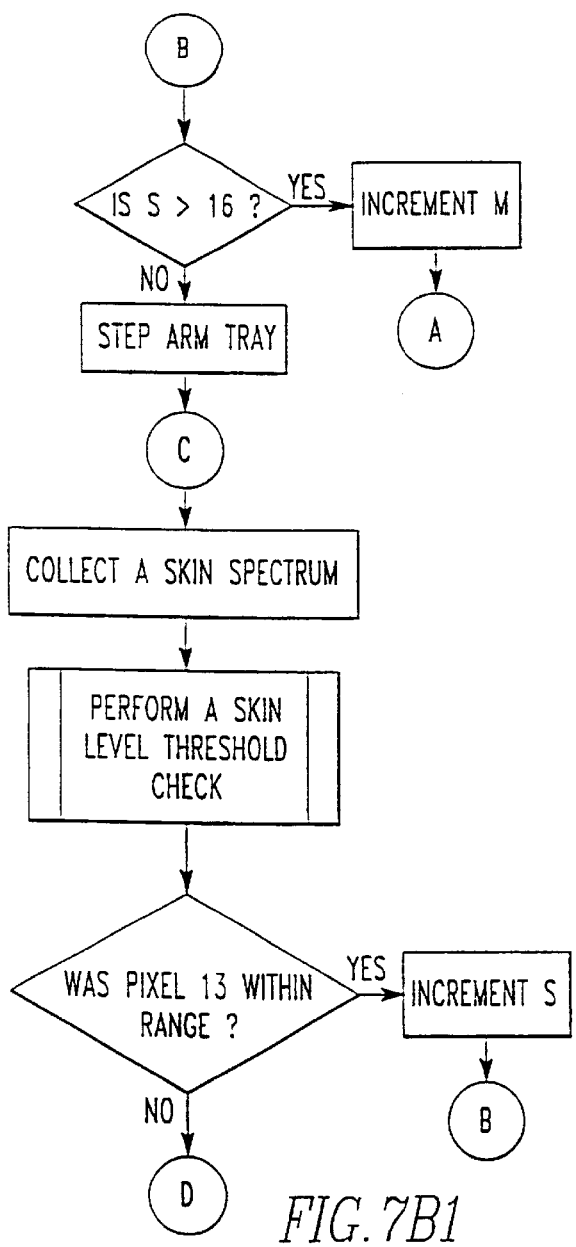
FIG. 7B1
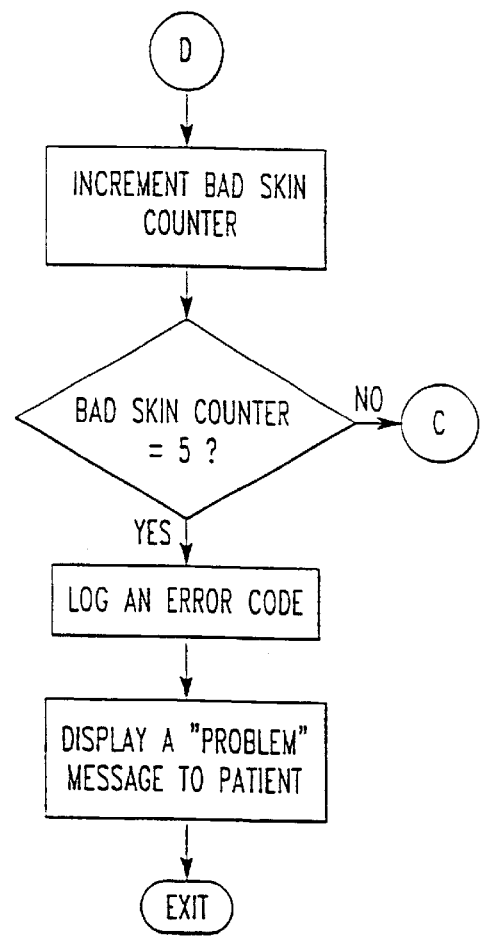
FIG. 7B2

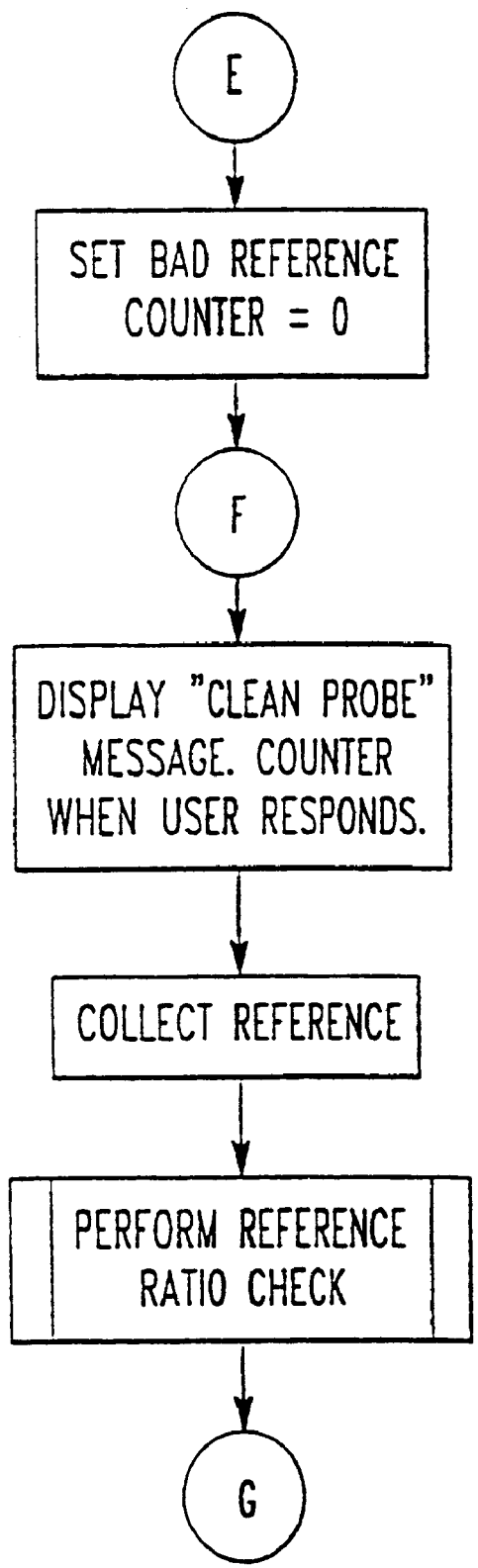
FIG. 7C1

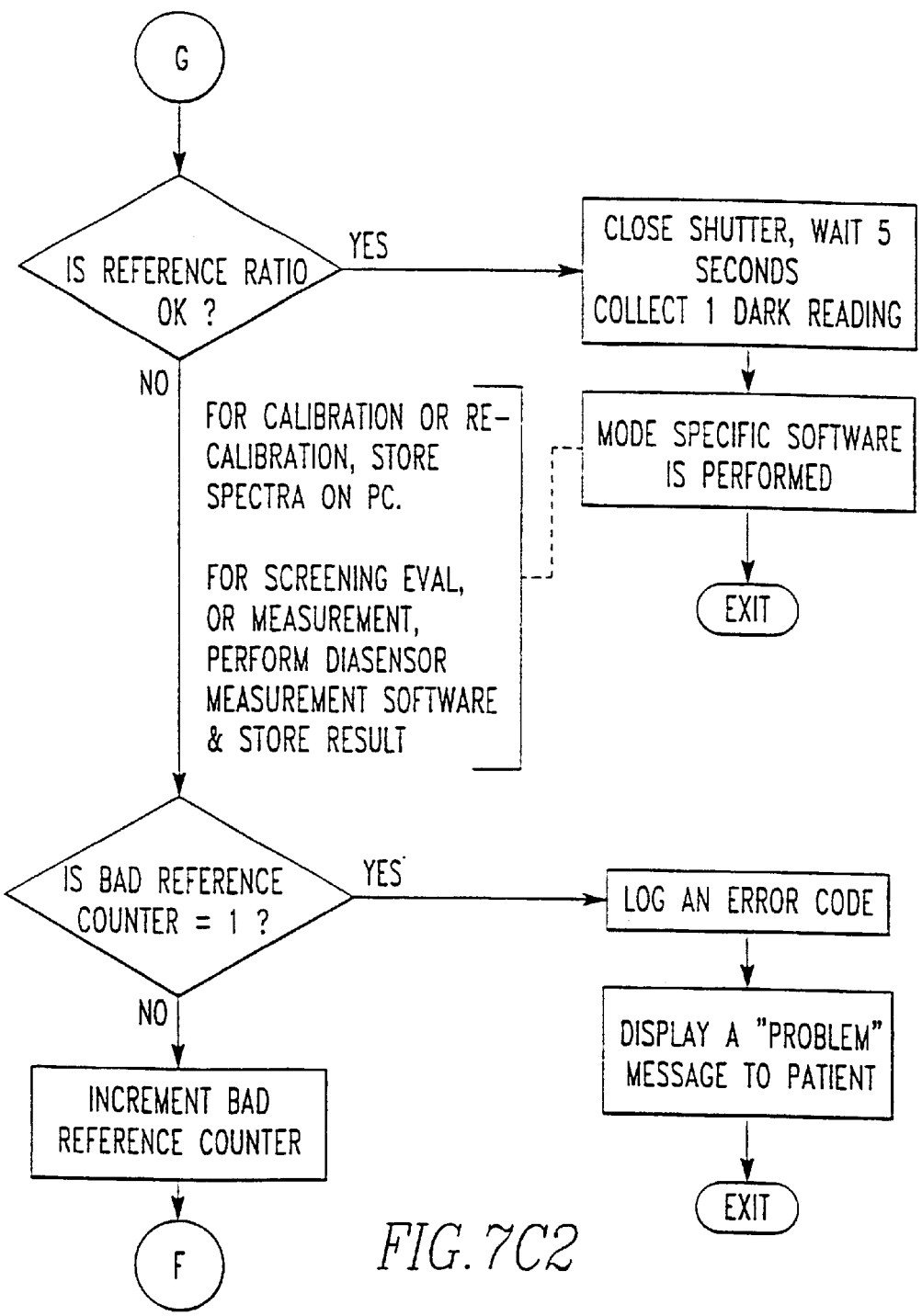
FIG. 7C2

INDIVIDUAL CALIBRATION OF BLOOD GLUCOSE FOR SUPPORTING NONINVASIVE SELF-MONITORING BLOOD GLUCOSE

CROSS-REFERENCE TO RELATED APPLICATION

This application claims priority to PCT/US98/03762, filed on Feb. 26, 1998, which, in turn, claims priority to provisional application Ser. No. 60/039,165, filed on Feb. 26, 1997.

BACKGROUND OF THE INVENTION

1. Field of the Invention

This invention relates to a process of calibrating a noninvasive blood glucose sensing monitor. In this invention, a process for calibrating a blood glucose monitor for an individual patient is described. This process provides a means for achieving the exquisite control or management of both signal as well as noise within the noninvasive measurement during calibration and subsequently during the long-term use of the calibrated device by humans desiring to monitor their level of blood glucose on demand.

2. Background Art

U.S. Pat. Nos. 5,070,874; 5,360,004; 5,379,764; 5,471,981; and 5,460,177 describe methods for the noninvasive measurement of blood glucose levels. In general, these methods use a spectrophotometer to measure the absorbance of near-infrared radiation at different wavelengths across the range of interest. The absorbance plotted against the wavelengths constitutes a spectrum. By analyzing the spectrum, the blood glucose levels, or changes thereto, can be determined. As the blood glucose levels vary, the detected spectrum also changes.

It is generally known that calibration of analytical devices can be accomplished through using univariate or multivariate mathematical/statistical analysis methodology. As such, reports of noninvasive blood glucose sensing have demonstrated the correlation of measurements of spectroscopic measurements obtained noninvasively with an alternative method known as a reference method requiring invasive and often painful sample collection. While much previous work deals with the process of calibration leading to interesting mathematical/statistical correlations, mathematical models have not yet been shown to be useful for reliable prospective glucose tests of a diabetic patient's blood glucose.

Previous reports on noninvasive glucose sensing have not proven that prospective noninvasive glucose determinations using these methods possess sufficient accuracy to allow the newly emerging technology to serve as a replacement of older invasive technology. By "prospective" testing, we mean that the glucose test results are followed forward in-time, allowing evaluation of long-term accuracy. Prospective testing involves evaluation and continuous monitoring of independent glucose tests as additional time lapses after first establishing the calibration. Previous reports have not demonstrated that the noninvasive technology can maintain model stability to the extent that these independent test results can remain accurate even as time elapses after the initial creation of the calibration model.

In previous calibration methods, data from numerous patients has been collected to calibrate a glucose monitor to a theoretical "norm". Test results from an individual patient were then compared to this norm to try to calculate that individual patient's glucose level. However, calibration using data obtained from a multitude of patients to prospectively measure glucose in any one patient has not been successful. This is mainly due to the large person-to-person variation in the morphology, physiology and chemistry of the skin.

Therefore, it is an object of the invention to provide a method of individually calibrating a noninvasive blood glucose sensing device to overcome the problems associated with patient-to-patient variability and also variability with an individual patient. It is also an object of the invention to provide a personalized calibration method that spans a patient's skin, spans time between readings and spans glucose variation inherent in a diabetic condition.

SUMMARY OF THE INVENTION

A method is provided for calibrating a noninvasive glucose monitor for prospective noninvasive glucose determination. Spectroscopic transflectance readings are measured on the patient's skin using a noninvasive glucose monitor. The patient's blood glucose level is measured with an invasive glucose monitor. The noninvasive and invasive measurements are correlated to form an individual algorithm for each patient.

Preferably, the position of the patient's skin with respect to the probe of the noninvasive monitor is spatially adjusted while collecting the transflectance measurements such that multiple readings are taken on the patient's skin. The measurements are preferably taken over a period of time and over a plurality of glucose levels in the patient.

A complete understanding of the invention will be obtained from the following description when taken in connection with the accompanying drawing figures.

DESCRIPTION OF THE DRAWINGS

FIGS. 5A1, 5A2, 5B1, 5B2, 5C1, 5C2, 5D, 5E, 5F1 and 5F2 are flow diagram showing a patient calibration procedure. In these flow diagrams, the process of data collection for calibration, verification and skin library development is shown. The skin library contains the patient's calibration algorithm, information about the control material and reference material. The prediction process makes use of the skin library to generate a patient's glucose test result;

FIGS. 6A1, 6A2, 6B1 and 6B2 show flow diagrams for collecting measurement data using a noninvasive monitor having a memory (PCMCIA) card. In order to demonstrate that the calibration can be used by a patient, the production of independent data should produce accurate and precise glucose test results. The prediction flow diagrams describe the use of the skin library components which are used in subsequent calculations leading to a glucose test result; and FIGS. 7A1, 7A2, 7B1, 7B2, 7C1 and 7C2 show flow diagrams for a noninvasive glucose monitor acquisition session.

DESCRIPTION OF THE PREFERRED EMBODIMENTS

Figure 1:
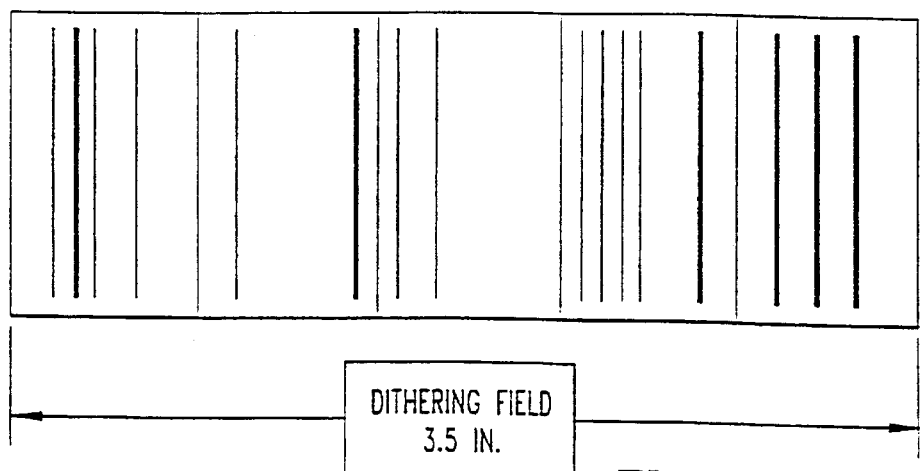
FIG. 1 shows a plot of a skin movement pattern for noninvasive data collection. In this plot, the skin movement over a stationary probe is indicated. A heavy bar represents an instance when the probe collects replicate readings at a fixed position on the skin. The term "replicate readings" means that the monitor took skin spectra repeatedly without moving the arm.

It is to be understood that the invention may assume various alternative variations and step sequences, except where expressly specified to the contrary. It is also to be understood that the specific devices and processes described in the attached drawings and the following specification are simply exemplary embodiments of the invention. Hence, specific time periods and other parameters related to the embodiments disclosed herein are not to be considered as limiting.

The present application pertains to the manner in which the data is collected to support an individual calibration for a noninvasive blood glucose monitor used by a particular patient. Only through careful calibration with and for each individual patient is it possible to achieve the accuracy and precision for prospective self-monitoring of blood glucose with a noninvasive monitor. Careful calibration involves managing three sources of variation: 1) patient-to-patient variation as previously described; 2) spatial variation arising from the heterogeneous nature of the skin within an individual patient; and 3) time-based variation that occurs as the patient undergoes changes in the biology of the cellular skin media or as the monitor device undergoes minute, diminutive changes in illumination signal strength, detector fluctuation and optical variation.

The noninvasive sensing of patient glucose variation depends on effective management of nuisance variation from these several sources. Since it is not practical to entirely eliminate all sources of variation, it is therefore necessary to manage nuisance variation judiciously. In this way, one can decrease the effect of nuisance variance when measuring glucose variation. The present invention accomplishes this by performing measurements controlled in both space and time.

The significant patient-to-patient variation prevalent in the prior art systems is made irrelevant by confining the calibration of the device to an individual patient. That is, for each patient who would use the device, a unique algorithm related to the measured response to glucose is determined from data obtained only from that patient.

Spatial adjustment referred to here occurs as motion is applied so that a relatively large area of the patient's skin is monitored, preferably through the use of an arm motion mechanism. The patient's arm is spatially adjusted with respect to the probe. However, similar adjustment may be realized by spatially adjusting the emitted light beam, whether or not through a probe, across the patient's skin. In addition, a larger area of the patient's arm can be illuminated, preferably simultaneously, with the light beam and multiple readings can be taken over this area while moving neither the probe(s) nor the patient's arm.

Temporal adjustment occurs as the patient continues to use the device during a multi-epoch period. An "epoch" refers to a period during which measurements occur, such as a calendar day. Multi-epoch measurements occur as the patient continues to make repeated readings on a daily basis over several days.

In accordance with the present invention, the patient's skin is measured with a noninvasive, infrared spectrometer. At the same time that these measurements are performed, the patient's blood glucose is measured with a highly accurate invasive method which is relied upon to yield a reference measurement of the patient's blood glucose. The mathematical correlation of the two measurements gives rise to an algorithm for that patient that can be used to provide an output consisting of a glucose reading by using an input to the mathematical equation consisting of the patient's spectroscopic measurement or spectrum.

The spectroscopic readings of the patient's skin are converted into glucose levels by using the patient's individual algorithm which relates future spectroscopic readings of the patient's skin to an associated glucose level. The conversion of spectral information into glucose concentration information is possible through using the mathematical algorithm previously determined as part of the calibration process. As the skin of a diabetic patient undergoes changes in glucose levels, i.e., as the patient's blood glucose level changes, the patient's spectroscopic measurements provide a fingerprint of the spectral characteristics during any specific time when a patient's glucose is at a new glucose level.

This invention pertains to the process of collecting sufficient data to support the successful calibration of an individual patient for self-monitoring of blood glucose with a noninvasive monitor. The data is considered to be sufficient after (a) satisfying a statistical sample size criterion and (b) achieving low correlation of glucose, as determined by the reference glucose determination method, with environmental sensors.

The method uses a two-epoch calibration system as a means for screening whether a patient can be calibrated. The first epoch is designed to provide calibration data. The second epoch is designed to provide verification data, whereby the data is used to verify whether the patient's individual calibration possesses the capability of providing accurate predictions of the patient's self-monitored blood glucose. In this way unsuccessful calibrations are screened out.

Turning to the data collection, the monitor uses a programmable skin movement pattern, an example of which is shown in FIG. 1, that can be adjusted to an individual patient's skin variation. The skin variation is determined by the mean and standard deviation of the skin spectra as a function of skin movement as described hereinbelow. The dithering field shown in FIG. 1 has a length of about 3.5 inches. Sampling over the dithering field helps compensate for the heterogeneity of the sampling medium.

The action of arm motion, while performing the process of individual calibration, provides a means of managing, or providing control over, spectral variability encountered when measuring the heterogeneous sample of the patient. Sampling variability can be described statistically by estimating the standard deviation spectrum from the arm measurement. The sample variance can be described as $s^2 = \Sigma(X - Xbar)^2/n-1$, where X is a vector measurement of the spectrum of the patient's skin transflectance and Xbar is the mean spectrum of n spectra taken to provide a test result. The magnitude of n can be determined by calculating the sample size in the manner described hereinafter. The pattern of movements effected on the arm consists of repeated short and long dither movements which are made in sequence when the device is in operation. Although the pattern is shown in FIG. 1 as having a specific pattern, this pattern may vary from time to time as the patient's skin undergoes changes. A successful readout is possible only if spatial adjustments are deployed on the patient's arm. This is due to the necessity of achieving a proper balance of sampling variability prior to rendering a patient's glucose readout. Further, the arm movement pattern is adjustable and can be optimized for each patient. As an example, bars of variable width are shown in FIG. 1. The width of the bar is proportional to the degree to which the sample has been replicated, i.e., that the arm has been repeatedly measured without moving the arm to a new location within the dithering field. As new measurements are made, each measurement must meet an acceptance criteria of goodness-of-fit before replication can proceed. If the goodness-of-fit criteria is met, then the process of replication proceeds. Goodness-of-fit can be accomplished by a number of acceptable methods, such as calculating the Euclidean or mahalanobis distance relative to previous skin measurements, vector correlation, or through use of linear discriminant analysis or use of lack-of-fit statistical analysis. The number of replicates increases until achieving no additional improvement in the sampling variance or until reaching a practical limit. The number of replicates and searching of new skin sites within the dithering field are a function of speed, which may vary as new hardware and software are tested.

After successful completion of the two-epoch calibration, the method uses a multi-epoch period of calibration data collection, which is necessary for collecting sufficient information for building a calibration that can predict a patient's blood glucose during in-home use, whereby the patient is making use of the monitor in their own home. A sufficient quantity is predetermined by calculating sample sizes for within- and between-day variation in skin spectral responses.

Figure 2:
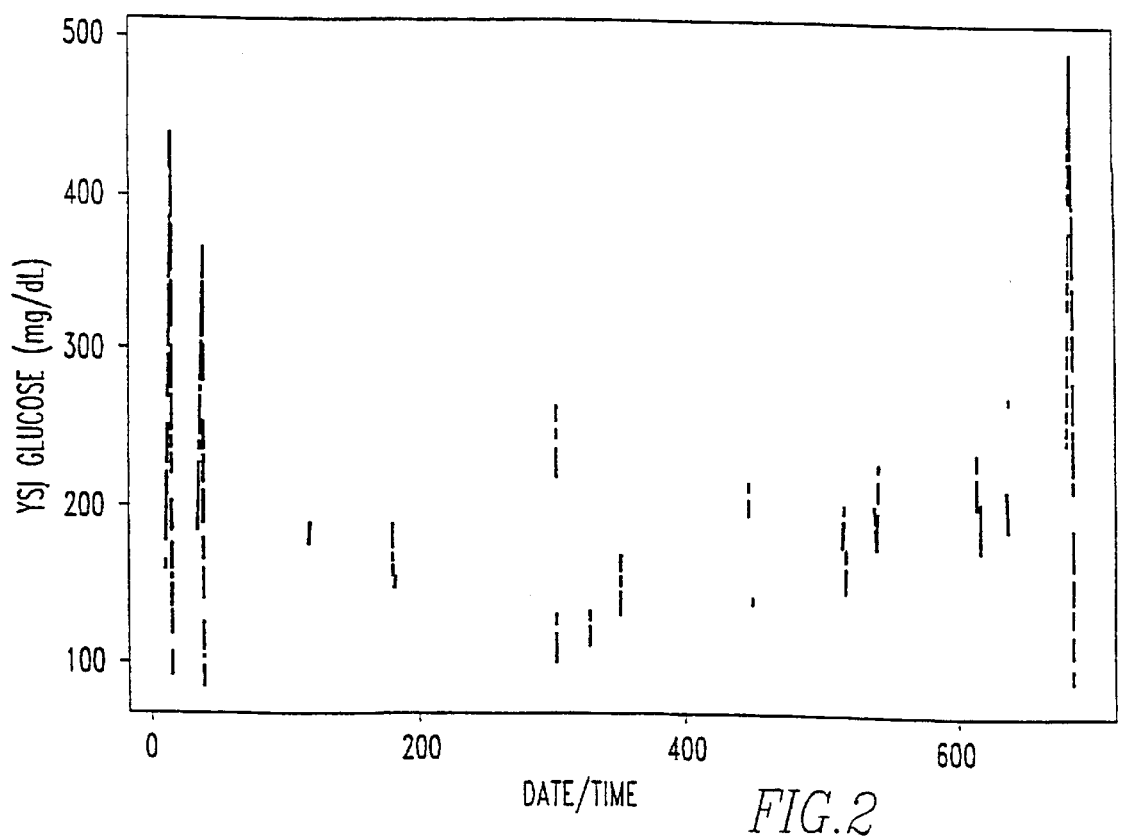
FIG. 2 is a plot of temporal history during multi-epoch calibration. In this plot the reference method reading (YSI) vs. time plot is shown. The points were taken in such a way as to provide low correlation of glucose (R<0.5) with environmental sensors. Sensors include temperature, humidity and barometric pressure. The correlation coefficient is calculated in the manner of the Pearson correlation coefficient.

As an example of how temporal adjustments are made, FIG. 2 illustrates how the adjustment of the glucose levels is performed over time. The y-axis shows the patient's blood glucose as determined by a highly accurate laboratory method, such as a Yellow Springs Instruments Blood Glucose Analyzer (YSI). This method makes use of the action of the glucose oxidase enzymatic reaction with the glucose molecules within the whole blood sample of the patient's blood, which then produces a read-out in glucose concentration having the units of mg/dL glucose. This value has an accuracy of <5% error {error=(actual-predicted)/actual*100} in the YSI concentration over the clinical range of the patient's calibration of <100 to >400 mg/dL. The x-axis shows the date/time index that has elapsed from the beginning of the calibration period. As an example, the x-axis index is a simple running index starting at 0 and counting upward, as time elapses from date/time=0 to date/time=650 (30 days). The maximum value on the x-axis in FIG. 2 corresponds to 30 days of data collection. For each patient the number of days may vary. The time period over which the time must elapse is determined by performing the calculation of statistical sample size discussed hereinafter. The sample size requires that the day-to-day variation is used in estimating the number of days required for calibration, where the number of days to be included in the calibration serves as a guide but may not need to be rigidly followed. The number of days required in the calibration data collection depends on the patient's daily variation throughout calibration. Usually, a successful calibration must span several days of variation to allow for daily variation, assumed to be prototypical of the patient's future, to occur and then allow for more robust model building.

Within FIG. 2, the placement of the YSI levels is chosen such that the YSI covariate is not significantly correlated with any of the environmental sensor covariates which are located within the noninvasive glucose case. The statistical model, which is used to test YSI and sensor covariates as being statistically insignificant, follows the form: $S=YB+E$, where S is the vector of sensor readings, Y is a vector of YSI readings, B is a vector of regression coefficients, and E is the unexplained variation within the model. The environmental sensors include: 1) ambient temperature, 2) probe temperature, 3) spectrograph temperature, 4) lamp temperature, 5) detector temperature, 6) ambient humidity and 7) barometric pressure. As data is collected from date/time=0, the YSI vs. environmental sensor correlation is continually updated until meeting the following criteria: a) an appropriate sample size is met and b) the sensor correlation is $r<0.5$ ($r$=Pearson correlation coefficient).

The calibration process typically involves two days of testing in a calibration center followed by several weeks of testing in the patient's home. The frequency of the readings during the two-day calibration, as well as the timing of the daily readings, is discussed below.

The monitor for implementation of this method preferably uses a programmable time sequence adjustable and adapted to the patient's changing spectroscopic skin readings as changes occur over time. The number of the patient's skin readings over time is adjusted after determining the between-day variation. The between-day variation is determined by calculating the mean and standard deviation of spectra over about two to seven days.

Figure 3:
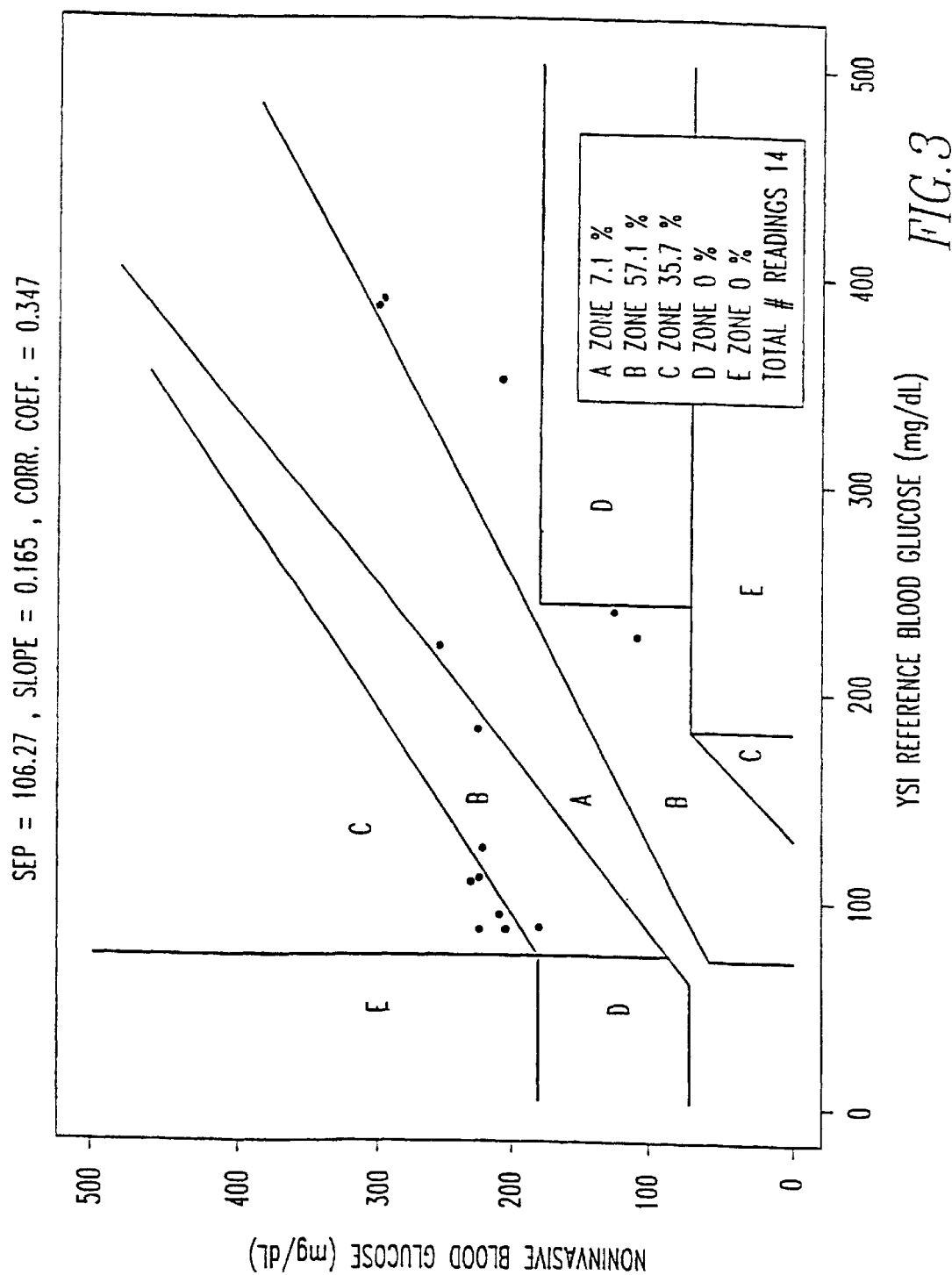
FIG. 3 is a plot of performance without spatio-temporal adaptation.
Figure 4:
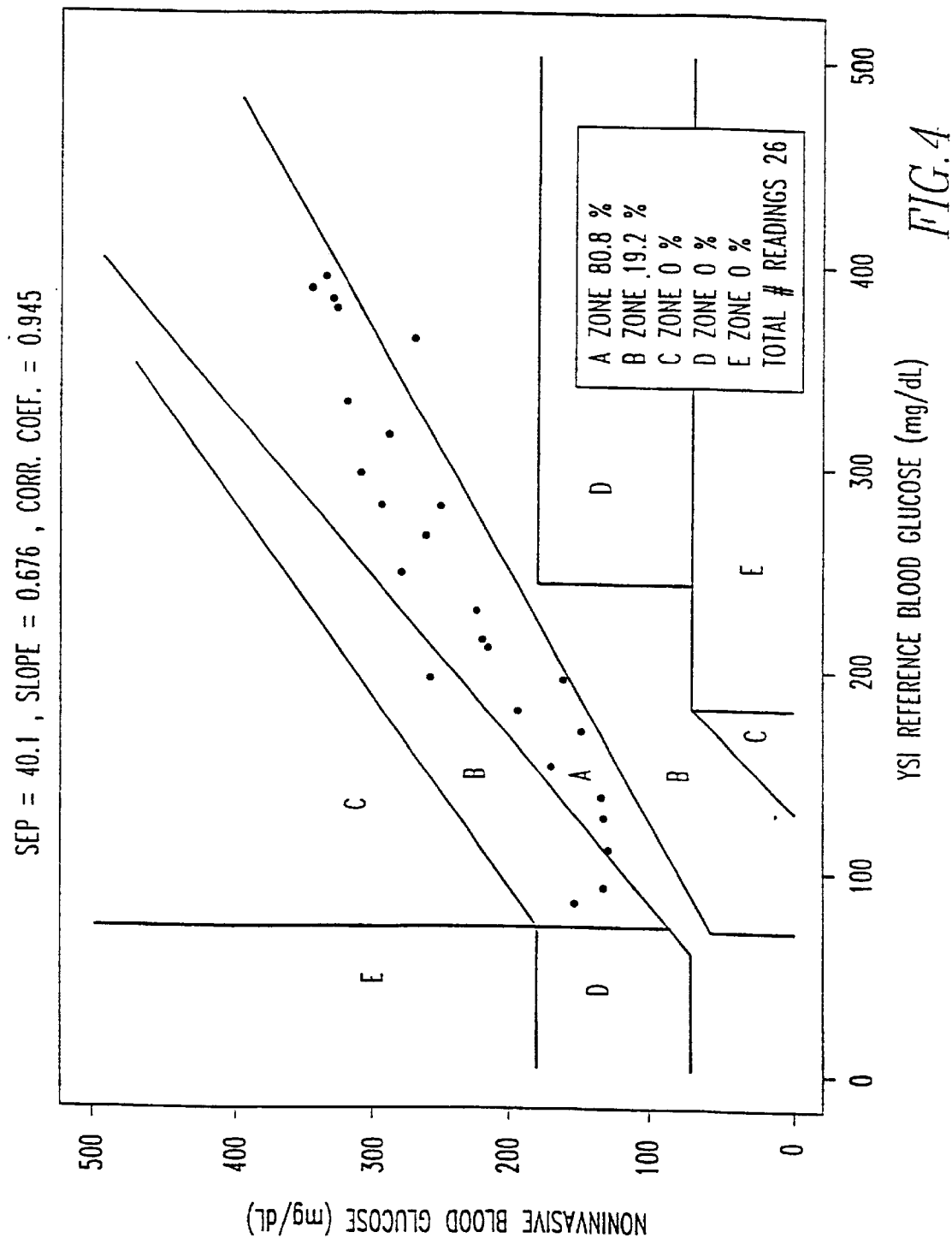
FIG. 4 is a plot showing the improved results after using spatio-temporal adaptation.

The use of adjustable spatial as well as temporal, i.e., spatio-temporal adjustments, allows for building a calibration for individuals. When using spatio-temporal adjustment during an individual calibration for each patient, the test results of noninvasive glucose readings are improved (FIGS. 3 and 4).

Thus, the present invention provides a method of collecting data from two devices of measure that provide paired measurements: i) measurements of the spectroscopic transflectance of a patient's skin and ii) measurements of a patient's blood glucose. The purpose of this is to provide a sufficient data set that can lead to a mathematical relationship supporting a self-monitored blood glucose test capability for an individual. The spectroscopic measurements are performed by a noninvasive blood glucose analyzer. The blood glucose analyzer will provide blood glucose levels having an accuracy of less than 5% error when compared to a laboratory method. The blood glucose analyzer is considered as a "reference" measurement of the true blood glucose value, and renders <5% error over a range of blood glucose from about 50 mg/dL to 400 mg/dL. Paired, longitudinal data is collected as the patient's blood is measured simultaneously with spectral data collection, preferably during a two-epoch period, to support an individual calibration for self-monitored blood glucose. The first of these epochs, such as is possible on the first of two days, is used to calibrate the monitor. The process of collecting the calibration data is described in FIGS. 5 and 7. The data is classified into a plurality of clusters of which each possesses a high degree of similarity of spectra assigned to a specific cluster. The relative spectral dissimilarity between clusters is large compared to similarity within a cluster. One or many clusters are used to describe prototypically acceptable or unacceptable data. The Euclidean distance between cluster centroids defining acceptable versus unacceptable ranges between about 0.5 to 1.5 Euclidean distance. A multivariate calibration is completed by using ordinary least squares, principal component regression or any other multivariate analysis technique to derive an equation of the form:

$$Y=XB+e$$

where Y is a vector of predicted glucose values, X is an n by m matrix of spectral responses, where n is the number of test results and m is the number of spectral variables, and B is a vector of least squares coefficients and e is a vector of errors.

The second of the two epochs, such as can be collected on the second consecutive day of two days, is used to verify the monitor. The procedure used to verify the predictive capability of the calibration is known as prediction and is shown in FIG. 6. The number of readings during these epochs shall be determined by a sample size determination criterion such as the following equation or any equation following the form:

$$N_{single-epoch} \geq Z\sigma/L$$

where N is the number of readings during the calibration. The number of spectroscopic measurements on the skin preferably meets or exceeds the value of N indicated in the above formula. The value of Z is approximated by the standard normal statistic, as obtained from a common table of calculated statistical values. The variable $\sigma$ is the measurement of the variation which represents the patient's skin variation. L is the value relating the desired clinical accuracy of the patient's skin variation.

A sample is collected to provide at least N measurements at each point in time that a patient's skin is adjusted to a new level of glucose. A new level of glucose is preferably achieved at such a rate of change as to provide enough time to acquire at least N measurements within a given glucose level. The glucose level associated with the N samples or measurements defines a discrete level of glucose that can be mathematically coupled to the state of the skin at a particular glucose concentration. The term "level" refers to an independent level of the patient's blood glucose which has been associated with an appropriate amount of spectroscopic samples of the patient's skin. A successful spectroscopic measurement will require sufficient signal to noise ratio, which can be achieved by striving for a high level of statistical power as to provide a representative sample of the patient's skin. Typically, the sample size supporting accurate glucose readings requires $\alpha=0.05$ and $\beta=0.1$.

The patient's skin variation is determined by deploying a skin movement mechanism on the patient's skin while simultaneously collecting the patient's spectroscopic transflectance measurements. The patient's skin variation is initially evaluated by determining the Pearson correlation coefficient "r" of the patient's newly acquired skin measurement with that of a previously determined skin spectrum. The previous skin measurement can be estimated from the training data by calculating the sample standard deviation in the manner previously described. Rules for skin movement are as follows: (1) only those skin readings passing r>0.95 are collected and stored in the memory of the monitor; (2) skin measurements having r<0.95 are followed by a large skin movement jump and do not require replicated measurements; (3) skin measurements having r>0.95 are replicated while continuing to monitor the value of r for each new measurement and recursively updating the estimate of the variance of the replicated measurements; and (4) replication ceases when the variance does not continue to improve or when reaching a time and/or memory limit.

The present process of calibration is preferably based on two-epoch adjustments of a patient's glucose, whereby adjustments are made by the usual means of therapy prescribed by the patient's physician. Increased blood glucose will be achieved by using a clinically acceptable method, such as the method of oral glucose loading, whereby the patient ingests a quantity of glucose such as needed to increase the patient's blood glucose level. The patient's glucose will be adjusted downward by an acceptable method of insulin therapy consistent with the patient's usual physician prescribed insulin therapy. The insulin therapy results in a downward adjustment in the patient's blood glucose. The patient's glucose excursion is defined as the difference between the highest and lowest level achieved during the calibration. The patient's glucose excursion preferably should exceed 200 mg/dL during the calibration process.

A diabetic's calibration algorithm is verified by testing the capability of the patient's individual algorithm to provide an accurate and precise reading of the patient's blood glucose test results from the patient on newly acquired data during the second epoch. Prediction frequency is preferably determined as prediction frequency=test results/attempts to obtain a test result*100%. Acceptable accuracy, precision and prediction frequency are as follows: accuracy and precision should support a standard error of prediction <30 mg/dL standard error for independent predictions over a period of time that the diabetic patient or patient's physician expects to use the monitor. Prediction frequency should be between 50–100%. Satisfactory accuracy, precision and prediction frequency performance are dependent on achieving the successful individual calibration; improvements in performance are possible by using multi-epoch calibrations. The number of epochs included in the multi-epoch calibration is determined in the same manner as the single-epoch expression. In the same way as with a single epoch, the value of a must be estimated. However, in this case it shall be an estimate of the between-day variation. Between-day variation shall be determined by performing measurements over several days (preferably ranging from a minimum of about three to as many as about seven days). The statistical estimates of the mean and standard deviation of the daily variation are used in a sample size determination, which is used to determine the duration of time over which the patient's spectral and blood glucose paired readings are performed. The sample size for the patient's temporal readings is determined by the following equation or by any equation having the form:

$$N_{multi-epoch}=Z\sigma/L$$

As a diagnostic evaluation of the quality of the calibration data, the correlation between glucose levels and environmental factors is determined. In the patient's multi-epoch data, the glucose variation is not correlated with the ambient temperature, skin temperature, internal temperature for any device internal-temperature sensor, or relative humidity and barometric pressure. In each case a correlation of r<0.5 is preferably determined for each sensor, where "r" is the Pearson correlation coefficient showing glucose correlation with the above-mentioned environmental sensors. When finding that the blood glucose reference values are correlated with any of the environmental sensors, yielding r>0.5, then additional data must be added to the patient's multi-epoch calibration such that the correlation coefficient can be driven to a level r<0.5.

EXAMPLE CALCULATIONS

Figure 5D:
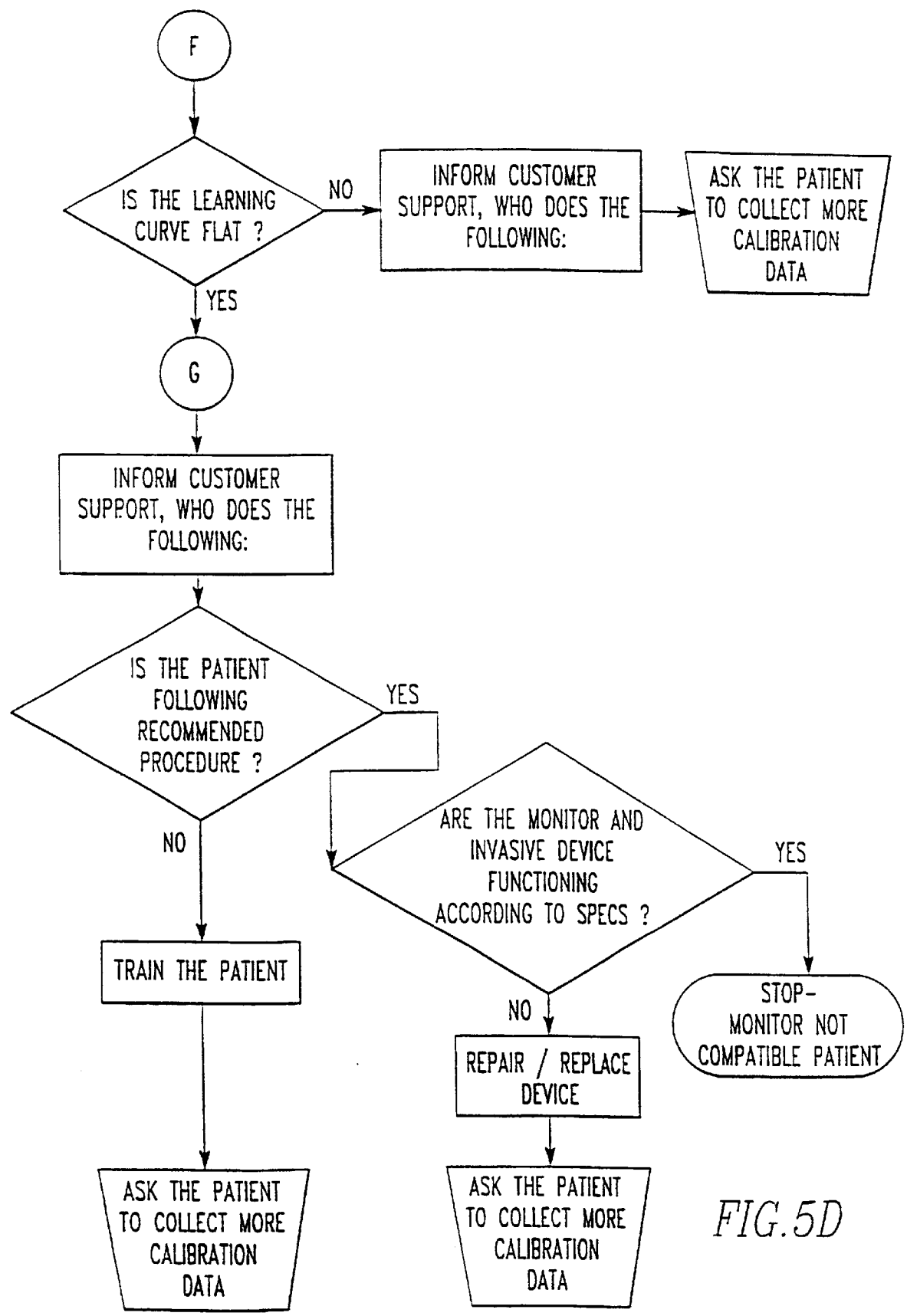
Figure 5E:
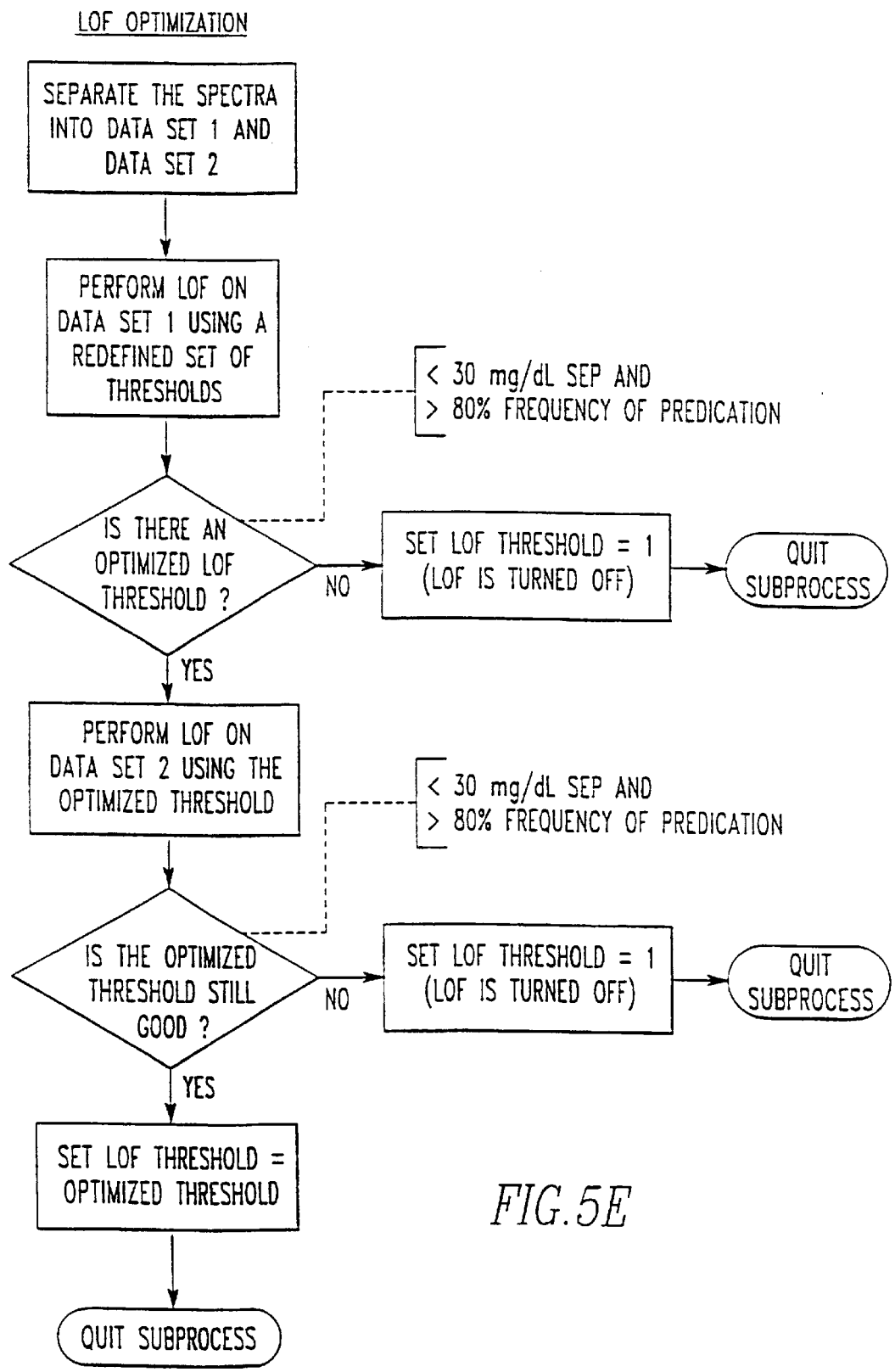

FIGS. 5–7 describe how data is collected and evaluated. While different analytical methods may be employed, the following are example mathematical analysis methods for the steps described in FIGS. 5–7:

Skin Level Threshold Check

The purpose of the skin level threshold check is to detect an open probe in the noninvasive monitor. For each skin spectra, the skin level threshold check is performed as follows:

1. Using a selected pixel, for example, pixel 13, compute a normalized floating-point pixel value $P_{NORM}$ in the range [0, 1].

2. If $P_{NORM}$ is in the range [0.3, 0.95], then accept the skin spectra. Otherwise, discard the skin spectra, increment the count of bad skin spectra and recollect the skin spectra at the same arm position.

3. If the total bad skin spectra count reaches five in a single session, reject the entire session.

Reference Ratio Check

The purpose of the reference ratio check is to detect a dirty probe on the monitor. In a session, skin spectra are bounded by two reference spectra denoted by $R_1$ and $R_2$, respectively. The reference ratio check is performed as follows:

1. Collect $R_1$, the skin spectra and then $R_2$.

2. Compute the average pixel values, $R_{1AVG}$ and $R_{2AVG}$, respectively.

3. If the ratio $R_{1AVG}/R_{2AVG} < 1.003$, accept the session. Otherwise, perform the following:

4. Prompt the user to clean the probe and collect $R_2$. Discard the original $R_2$.

5. Compute the average pixel value $R_{2AVG}$.

6. If the ratio $R_{1AVG}/R_{2AVG} < 1.003$, accept the session. Otherwise, reject the entire session.

Standard Deviation Check

The standard deviation check is performed on a set of skin spectra. Let M denote the number of skin spectra in the set. Let $S_{ij}$ denote a particular skin spectra pixel, where i denotes the spectra number $\{1 \ldots M\}$ and j denotes the pixel number $\{1 \ldots 64\}$. The standard deviation check is performed as follows:

1. Compute standard deviations of individual pixels: $\sigma_j = \text{STDEV}(S_{1j}, S_{2j}, \ldots S_{Mj})$ for j=1 to 64.

2. Compute the average of the 64 standard deviations, denoted as $\sigma_{AVG}$.

3. If $\sigma_{AVG} < 0.008$, accept the session. Otherwise, reject the session.

Lack-of-Fit (LOF) Test and Optimization

Skin absorbance spectra passes the LOF test if the following is true.

$$F_p < F_c$$

$F_c$ is the critical F statistic for a given level of significance and degrees of freedom $$F_p = \frac{s_p^2}{s_o^2}$$

$s_o^2$ mean of calibration spectral residual vector squared norm $s_p^2$ squared norm of prediction spectral residual vector $s_o^2$ (computed only once)

$$s_o^2 = \frac{\sum_{i=1}^{n} e_i^2}{(n - r - 1)(m - r)}$$

$e_i^2$ squared norm of spectral residual for calibration vector, i $$e_i^2 = \tilde{x}_i^T W_{r+1} W_{r+1}^T \tilde{x}_i$$

$\tilde{x}_i$ mean-centered calibration spectra

W the PLS "eigenvectors" in the wavelength domain (from Lanczos bidiagonal decomposition, $X = PBW_T$)

$W_{r+1}$ the last (r+1) to m column vectors of W that span the "noise" subspace r rank (=25)

m number of channels n number of spectra in the calibration set $s_p^2$ (computed for each prediction spectrum, p)

$$s_p^2 = \frac{e_p^2}{(m - r)}$$

$e_p^2$ squared norm of spectral residual for prediction vector, p $$e_p^2 = \tilde{x}_p^T W_{r+1} W_{r+1}^T \tilde{x}_p$$

$\tilde{x}_p$ prediction spectrum mean-centered to calibration set

For example, if r=25; m=43; and n=200, $F_c=1.58$ at 0.05 level of significance. Therefore, if $F_p < 1.58$, the prediction spectrum p passes the LOF test.

LOF threshold, T=(1-level of significance). Optimize LOF threshold as follows:

During weeks seven and eight of calibration, develop LOF threshold by the following procedure:

Using the first six weeks of data and self-prediction, perform LOF threshold optimization. If a threshold T can be found such that SEC<30 mg/dL and % Prediction>80%, use this value of T (else, T=1.0). Using data from weeks seven and eight, using threshold=T, confirm that SEP<30 mg/dL and % Prediction>80%. If not, set T=1.0.

PLS Decomposition

1. Transform the Matrix $X_{avg}$

The purpose of PLS decomposition is to produce regression coefficients from the mean-centered absorbance spectra and invasive readings provided. Use the bidiagonalization algorithm described below to transform the matrix $X_{avg}$ to rank p into three matrices, $UBV^T$, using $Y_{avg}$.

| | |
|---|---|
| p | rank used |
| m | number of channels used +1 for the interpolated glucose value (number of columns) |
| n | number of spectra (number of rows) |
| X | an n by m matrix |
| $X_{avg}$ | a matrix that contains mean-centered spectral data from the X matrix |
| $Y_{avg}$ | a vector containing mean-centered glucose values |
| rank p | the number of factors actually used in the bidiagonalization function |

-continued

| | |
|---|---|
| U | an n by p orthogonal matrix whose columns contain PLS scores, projections into n dimensional space that are themselves derived from the spectra and glucose (X and Y matrices, respectively). The PLS scores show normalcy and outliers in spectra. |
| B | a p by p diagonal-superdiagonal matrix having nonzero elements on the diagonal and the superdiagonal; the elements demonstrate the magnitude of the PLS scores |
| V | a p by m orthonormal matrix whose columns are the basis vectors of the column space of $X_{avg}$ and whose rows are the loadings, which demonstrate the importance of each column of $X_{avg}$. |

2. The Algorithm for Bidiagonalization

The bidiagonalization algorithm uses the $Y_{avg}$ vector to transform the matrix $X_{avg}$ for each rank up to p rank into three matrices, $UBV^T$. This algorithm is presented below. The lower case letters represent a column of a matrix. The subscript represents the particular element. Some basic terms:

$u_j$ $j^{th}$ PLS scores or $j^{th}$ column of U
$v_j$ $j^{th}$ column of V
$q_j$ pre-normalized $v_j$
$p_j$ pre-normalized $u_j$
$\alpha_j$ $j^{th}$ diagonal of B
$\beta_j$ $j^{th}$ superdiagonal of B The steps of the algorithm follow.

1a. Mean center to get $X_{avg}$ and $Y_{avg}$
1b. Compute the starting vector, $q_1 = X_{avg}^T Y_{avg}$ (use to maximize correlation)
1c. Compute $v_1 = q_1/\|q_1\|$
1d. Compute $p_1 = X_{avg} v_1$ Then, for each rank, 1 through p, compute the following.

2. Compute $u_j = p_j/\|p_j\|$
3. Column j of $V = v_j$. Column j of $U = u_j$. (builds one column of each matrix, V and U, for each rank)
4. $\alpha_j = j^{th}$ diagonal of B = norm of $p_j$ (builds one diagonal of matrix B for each rank)
5. $q_{j+1} = u_j^T X_{avg} - \alpha_j v_j$ Perform modified Gram-Schmidt algorithm to insure $v_j$ is orthogonal to the other columns of V.

6. $\beta_j = j^{th}$ superdiagonal of B = norm of $q_{j+1}$
7. Compute $v_{j+1} = q_{j+1}/\|q_{j+1}\|$
8. $p_{j+1} = X_{avg} v_{j+1} - \beta_j u_j$
9. Let j=j+1 and go to Step 2.

Stop this procedure when either the norm of q=0 or when j is greater than rank p.

$$X_{avg} = UBV^T$$

$$X_{avg}V = UBV^T V$$

since we are using an orthonormal basis, $$V^T V = I_p$$

so $$X_{avg}V = UB \quad (6)$$

By fundamental linear algebra, $A_{ei}$ = the $i^{th}$ column of any matrix A and $e_i^T A$ = the $i^{th}$ row of A, where e is the elemen tary matrix. This can be applied since it has been established that B is a diagonal-superdiagonal matrix. Therefore, $$Be_i = \beta_{i-1} e_{i-1} + \alpha_i e_i \text{ for } i>1, \text{ and} \quad (7)$$

$$e_i^T B = \alpha_i e_i^T + \beta_i e_{i+1} \text{ for } i<n \quad (8)$$

Using equations 7 and 8 to substitute in the decomposition, equations for $\alpha_i$ and $\beta_i$ can be obtained. The following is the derivation of equations for $\alpha_j$ and $\beta_j$, which give the equations for $P_{j+1}$ and $q_{j+1}$:

| $\alpha_j$ | $\beta_j$ |
|---|---|
| $X_{avg}V = UB$ | $U^T X_{avg} = BV^T$ |
| $X_{avg}Ve_i = UBe_i$ | $X_{avg}^T U = VB^T$ |
| $X_{avg}Ve_i = U(\beta_{i-1}e_{i-1} + \alpha_i e_i)$ | $X_{avg}^T Ue_i = VB^T e_i$ |
| $X_{avg}V = U\beta_{i-1}e_{i-1} + U\alpha_i e_i$ | $X_{avg}^T U = V(\alpha_i e_i^T + \beta_i e_{i+1})$ |
| $U\alpha_i e_i = X_{avg}V - U\beta_{i-1}e_{i-1}$ | $X_{avg}^T U = V\alpha_i e_i^T + V\beta_i e_{i+1}$ |
| $P_{j+1} = X_{avg}V - U\beta_{i-1}e_{i-1}$ (9) | $V\beta_i e_{i+1} = X_{avg}^T U - V\alpha_i e_i^T$ |
| | $q_{j+1} = X_{avg}^T U - V\alpha_i e_i^T$ (10) |

Randomized Bin-Averaging (RBA) Calibration Method

Start with approximately 120 sittings×6 sessions×4 subsessions=2,880 absorbance spectra available for calibration. Randomly pick three out of 2,880 spectra. Make sure not to include the same spectrum twice. Form a "linear combo spectrum" by adding the three up going "++−" on both their absorbance and their invasive readings. Replace the three picked spectra back into the population of 2,880. Sort the invasive readings of the linear combo spectrum into one of ten different glucose bins: first bin is from 0–40 mg/dL, the second is from 40–80 mg/dL, . . . , tenth bin is from 360–400 mg/dL. Discard those linear combo spectra which have invasive readings of <0 mg/dL or >400 mg/dL. Repeat until each glucose bin contains at least 30×90 =2,700 linear combo spectra. Within each glucose bin, form thirty averages over ninety (ntavg=90) linear combo spectra. These averages constitute the population of 10 bins×30 averages=300 calibration spectra. Perform PLS (rank=25) using the 300 calibration spectra and obtain the calibration vector. Use this calibration vector for obtaining monitor measurements in the period succeeding the calibration period.

Slope and Intercept Correction (SIC) Calibration Method

1. Perform PLS (rank=25) using the 2,880 spectra (approx.) available and obtain the calibration vector.
2. Perform "self-prediction" whereby the calibration spectra are used to obtain monitor$_c$ measurements which are regressed against the corresponding invasive reading values ($HQ_c$).

$$Monitor_c = k_1*(HQ_c) + k_0$$

3. Use the calibration vector from step 1 for obtaining monitor measurements in the period succeeding the calibration period and apply the following correction using $k_0$, the calibration intercept and $k_1$, the calibration slope. The corrected prediction $$Monitor^{SIC} = (Monitor - k_0)\frac{1}{k_1}$$

Procedure for Selection Between SIC and RBA Calibration Methods for Each Patient Split 60-day calibration data into Set 1 (six week approx.) for calibration and Set 2 (two weeks approx.) for testing. Select the method which performs better on the following tests (in descending order of importance) using Set 2 predictions:
1. hypothesis tests of equality of slope to 1 and intercept to 0
2. closeness of slope to 1
3. smallness of SEP Quality Monitoring Cutoff Value The purpose of the quality monitoring cutoff value is to provide the patient with a threshold under which the difference between the monitor measurement and invasive reading value has to lie for quality control purposes. For paired monitor measurement ($x_i$) and invasive value ($y_i$) for data collected during calibration define a root mean square (RMS) error as follows:

$$RMS = \sqrt{\frac{1}{M}\sum_{i=1}^{M}(y_i - x_i)^2}$$

where M is the number of paired results QM cutoff value= 2·RMS

Control Standard Check

The purpose of the control standard check is to identify any gross malfunction of the monitor due to conditions, such as dirty probe, lamp outage, etc. The following steps are performed for the control standard check.

1. Collect risk analysis hazard data for a patient's device or transfer prototypical hazard data from monitor risk analysis testing.
2. Collect calibration data from population of N subjects. Calibration data shall consist of spectral readings of patient skin and control standard material and reference blood glucose monitoring device. The control standard material shall have a stated target concentration and the target concentration from each lot of control material shall be provided by manufacturing.
3. Use analysis of variance (ANOVA) to determine control limits. If as many as four patients will use a single device at several sites, then use the nested analysis of variance as follows:

$$R_{ij} = \tau_i + \beta_i + \epsilon_{ij}$$

where $\tau$ is site and $\beta$ is patient within site. The "Root MSE" from ANOVA modeling allows us an estimate of the control limits to be applied to future patients.

4. Determine the control limit as: (CL)=3(Root MSE)
5. Determine upper control limit as:
   Upper=Target Glucose Concentration+CL
6. Determine lower control limit as:
   =Lower Target Glucose Concentration−CL
7. Append to the patient's calibration data all control readings during the calibration period.
8. Determine control material calibration vector from appended data.
9. Apply control material calibration vector to both the control readings and patient skin readings during the calibration period.
10. Apply control material calibration vector to risk and hazard data.
11. Select the calibration vector rank by optimizing the performance of the calibration vector. Optimal performance is such that we maximize the control material readings falling within the control limits during calibration and also maximize the number of control material readings falling out when testing hazard data.

Thus, as will be understood by one of ordinary skill in the art, the present invention provides a method of calibrating a noninvasive glucose monitor for an individual patient which overcomes the problems associated with previously known calibration methods. The disclosed method provides a personalized calibration method that spans a patient's skin, the time between readings and the glucose variation inherent in a diabetic condition.

It will be readily appreciated by those skilled in the art that modifications may be made to the invention without departing from the concepts disclosed in the foregoing description. Such modifications are to be considered as included within the following claims unless the claims, by their language, expressly state otherwise. Accordingly, the particular embodiments described in detail herein are illustrative only and are not limiting to the scope of the invention which is to be given the full breadth of the appended claims and any and all equivalents thereof.

We claim:

1. A method of calibrating a noninvasive glucose monitor for prospective noninvasive glucose determination, comprising the steps of:
   measuring spectroscopic transflectance readings of a patient's skin using a noninvasive glucose monitor;
   measuring the patient's blood glucose level with an invasive glucose monitor;
   correlating the noninvasive and invasive measurements to form an individual algorithm for the patient; and
   spatially adjusting a position of the patient's skin with respect to a probe of the noninvasive glucose monitor while collecting transflectance measurements such that multiple readings are taken over a relatively large area of the patient's skin.

2. The method as claimed in claim 1, including taking noninvasive and invasive measurements over at least a two-epoch period.

3. The method as claimed in claim 2, including using the noninvasive and invasive measurements from the first epoch to calibrate the noninvasive monitor.

4. The method as claimed in claim 2, including using the measurements from the second epoch to determine the patient's glucose level.

5. The method as claimed in claim 2, wherein the number of transflectance readings is determined by the formula $N \geq Z\sigma/L$, where N is the number of readings during calibration, Z is approximated by the standard normal statistic, $\sigma$ represents the patient's skin variation and L relates to a desired clinical accuracy of the patient's skin variation.

6. The method as claimed in claim 2, including adjusting the number of transflectance measurements over time after determining a between-epoch variation between transflectance measurements.

7. The method as claimed in claim 6, including determining the between-epoch variation between transflectance measurements by calculating the mean and standard deviation of spectra over about two to seven days.

8. The method as claimed in claim 2, wherein the first epoch lasts for a period of about 2–60 days.

9. The method as claimed in claim 1, including taking noninvasive and invasive measurements over a plurality of glucose levels in the patient.

10. The method as claimed in claim 1, including converting the spectroscopic transflectance readings to glucose levels using the individual algorithm.

11. The method as claimed in claim 1, including replicating the transflectance measurements until there is no improvement in sampling variance.

12. The method as claimed in claim 1, including spatially adjusting the position of the patient's skin or the probe by a plurality of dithering movements.

13. The method as claimed in claim 1, including taking multiple transflectance measurements in a pattern on the patient's skin.

14. The method as claimed in claim 1, wherein the transflectance readings of the patient's skin are taken by illuminating an area of the patient's skin and taking multiple transflectance readings over this area.

15. A method of calibrating a noninvasive glucose monitor for prospective noninvasive glucose determination, comprising the steps of:

measuring spectroscopic transflectance readings of a patient's skin using a noninvasive glucose monitor;

measuring the patient's blood glucose level with an invasive glucose monitor;

correlating the noninvasive and invasive measurements to form an individual algorithm for the patient;

spatially adjusting a position of the patient's skin with respect to a probe of the noninvasive glucose monitor while collecting transflectance measurements such that multiple readings are taken over a relatively large area of the patient's skin;

taking noninvasive and invasive measurements over at least a two-epoch period;

taking noninvasive and invasive measurements over a plurality of glucose levels in the patient; and converting the spectroscopic transflectance readings to glucose levels using the individual algorithm.

16. The method as claimed in claim 15, including spatially adjusting the position of the patient's skin or the probe by a plurality of dithering movements.

17. The method as claimed in claim 15, including taking multiple transflectance measurements in a pattern on the patient's skin.

18. The method as claimed in claim 15, including using the noninvasive and invasive measurements from the first epoch to calibrate the noninvasive monitor.

19. The method as claimed in claim 15, including using the measurements from the second epoch to determine the patient's glucose level.

20. A method of calibrating a noninvasive glucose monitor for prospective noninvasive glucose determination, comprising the steps of:

measuring spectroscopic transflectance readings of a patient's skin using a noninvasive glucose monitor;

measuring the patient's blood glucose level with an invasive glucose monitor;

correlating the noninvasive and invasive measurements to form an individual algorithm for the patient;

spatially adjusting a position of the patient's skin with respect to a probe of the noninvasive glucose monitor while collecting transflectance measurements such that multiple readings are taken over relatively large area of the patient's skin;

taking noninvasive and invasive measurements over at least a two-epoch period;

taking noninvasive and invasive measurements over a plurality of glucose levels in the patient;

converting the spectroscopic transflectance readings to glucose levels using the individual algorithm;

spatially adjusting the position of the patient's skin or the probe by a plurality of dithering movements;

taking multiple transflectance measurements in a pattern on the patient's skin;

using the noninvasive and invasive measurements from the first epoch to calibrate the noninvasive monitor; and using the measurements from the second epoch to determine the patient's glucose level.

* * * * *

UNITED STATES PATENT AND TRADEMARK OFFICE
CERTIFICATE OF CORRECTION

PATENT NO. : 6,309,884 B1
DATED : October 30, 2001
INVENTOR(S) : Patrick J. Cooper et al.

Page 1 of 1

It is certified that error appears in the above-identified patent and that said Letters Patent is hereby corrected as shown below:

Column 2,
Line 57, "diagram" should read -- diagrams --.
Line 67 "production" should read -- prediction --.

Column 8,
Lines 33-34 "value of a" should read -- value of σ --.

Column 12,
Line 18, under column headed "$\beta_j''$", fourth row, text within parentheses: delete "=" and insert -- + --; and fifth row, text within parentheses: delete "=" and insert -- + --.

Signed and Sealed this

Twenty-eighth Day of May, 2002

Attest:

Attesting Officer

JAMES E. ROGAN
Director of the United States Patent and Trademark Office